(12) United States Patent
Blouin et al.

(10) Patent No.: US 9,543,523 B2
(45) Date of Patent: Jan. 10, 2017

(54) CYCLOHEXADIENE FULLERENE DERIVATIVES

(71) Applicants: MERCK PATENT GMBH, Darmstadt (DE); Nano-C, Inc., Westwood, MA (US)

(72) Inventors: Nicolas Blouin, Southampton (GB); Stephane Berny, Southampton (GB); Edward A. Jackson, Ayer, MA (US); Henning Richter, Newton, MA (US); Feng He, Chicago, IL (US)

(73) Assignees: MERCK PATENT GMBH, Darmstadt (DE); NANO-C, INC., Westwood, MA (US)

( * ) Notice: Subject to any disclaimer, the term of this patent is extended or adjusted under 35 U.S.C. 154(b) by 90 days.

(21) Appl. No.: 14/483,488

(22) Filed: Sep. 11, 2014

(65) Prior Publication Data
US 2015/0069304 A1 Mar. 12, 2015

Related U.S. Application Data

(60) Provisional application No. 61/876,427, filed on Sep. 11, 2013.

(51) Int. Cl.
| | | |
|---|---|---|
| *H01L 51/00* | (2006.01) | |
| *C07C 43/215* | (2006.01) | |
| *C07C 13/62* | (2006.01) | |
| *C07D 333/08* | (2006.01) | |
| *H01L 51/42* | (2006.01) | |

(52) U.S. Cl.
CPC ........... *H01L 51/0047* (2013.01); *C07C 13/62* (2013.01); *C07C 43/215* (2013.01); *C07D 333/08* (2013.01); *C07C 2104/00* (2013.01); *H01L 51/0036* (2013.01); *H01L 51/0094* (2013.01); *H01L 51/4253* (2013.01); *Y02E 10/549* (2013.01); *Y02P 70/521* (2015.11)

(58) Field of Classification Search
CPC .................................................. H01L 51/0047
USPC ............... 252/500; 549/59; 568/643; 585/25
See application file for complete search history.

(56) References Cited

U.S. PATENT DOCUMENTS

| | | | | |
|---|---|---|---|---|
| 7,396,520 B2* | 7/2008 | Howard | ................. | B82Y 30/00 423/445 B |
| 8,697,988 B2* | 4/2014 | Laird | ..................... | B82Y 10/00 136/244 |
| 8,715,606 B2* | 5/2014 | Laird | ..................... | B82Y 10/00 252/502 |
| 8,952,247 B2 | 2/2015 | Sato et al. | | |
| 2011/0005597 A1 | 1/2011 | Sato et al. | | |
| 2012/0004476 A1 | 1/2012 | Yoon et al. | | |
| 2015/0207076 A1* | 7/2015 | Tierney | ................ | C07D 495/04 252/500 |
| 2015/0340616 A1* | 11/2015 | Blouin | ..................... | C08K 3/04 252/500 |
| 2015/0353575 A1* | 12/2015 | Mitchell | .............. | C07D 495/04 549/43 |

FOREIGN PATENT DOCUMENTS

| | | |
|---|---|---|
| EP | 2175502 A1 | 4/2010 |
| EP | 2392555 A2 | 12/2011 |
| KR | 101128833 B1 | 3/2012 |
| WO | 2011160021 A2 | 12/2011 |

OTHER PUBLICATIONS

Written Opinion for PCT/EP2014/002210, mailed Dec. 2, 2014.*
International Search Report for PCT/EP2014/002210 dated Dec. 2, 2014.
Durdagi, S. et al., "Computational design of novel fullerene analogues as potential HIV-1 PR inhibitors: Analysis of the binding interactions between fullerene inhibitors and HIV-1 PR residues using 3D QSAR, molecular docking and molecular dynamics simulations," Bioorganic & Medicinal Chemistry, 2008, vol. 16, pp. 9957-9974.
Periya, V. K. et al., "Hydrophilic [60]fullerne carboxylic acid derivatives retaining the original 60-π electronic system," Tetrahederon Letters, 2004, vol. 45, pp. 8311-8313.
Liou, K. et al., "Cyclotrimerization of Alkynes with [60]Fullerene in the Presence of Tricyclohexylphosphine," J. Chem. Soc., Chem. Commun., 1995, pp. 1603-1604.
An, Y. et al., "A methodology for the reversible solubilization of fullerenes," J. Org. Chem., 1995, vol. 60, pp. 6353-6361.
Cossu, S. et al., "Unexpected Formation of Dienes in the Diels-Alder Reaction of Exocyclic 1-Bromobutadienes of Polycyclic Hydrocarbons," J. Org. Chem., 1996, vol. 61, pp. 153-158.
Hsiao, T. et al., "Nickel-Promoted First Ene-Diyne Cycloaddition Reaction of C60: Synthesis and Photochemistry of the Fullerene Derivatives," J. Am. Chem. Soc., 1998, vol. 120, pp. 12232-12236.
Qian, W. et al., "C62, a Non-Classical Fullerene Incorporating a Four-Membered Ring," J. Am. Chem. Soc., 2000, vol. 122, pp. 8333-8334.
Inoue, H. et al., "A novel and practical synthesis of alkoxycarbonyl-substituted bis(fulleroid)," Synlett, 2000, vol. 8, pp. 1178-1180.
Iwamatsu, S. et al., "A Novel Photorearrangement of a Cyclohexadiene Derivative of C60," Organic Letters, 2002, vol. 4, No. 7, pp. 1217-1220.

(Continued)

*Primary Examiner* — Douglas McGinty
(74) *Attorney, Agent, or Firm* — Millen, White, Zelano, Branigan, P.C.

(57) ABSTRACT

The invention relates to novel fullerene derivatives, to methods for their preparation and educts or intermediates used therein, to mixtures and formulations containing them, to the use of the fullerene derivatives, mixtures and formulations as organic semiconductors in, or for the preparation of, organic electronic (OE) devices, especially organic photovoltaic (OPV) devices and organic photodetectors (OPD), and to OE, OPV and OPD devices comprising, or being prepared from, these fullerene derivatives, mixtures or formulations.

28 Claims, 1 Drawing Sheet

(56) References Cited

OTHER PUBLICATIONS

Vida, Y. et al., "Electropolymerizable Terthiophene S,S-Dioxide-Fullerene Diels-Alder Adduct for Donor/Acceptor Double-Cable Polymers," Macromolecular Rapid Commun., 2007, vol. 28, pp. 1345-1349.
Nambo, M. et al., "Aziridinofullerene: A Versatile Platform for Fictionalized Fullerenes," Journal of the American Chemical Society, 2011, vol. 133, pp. 2402-2405.
English Abstract of KR-101128833, Publication Date: Mar. 27, 2012.

* cited by examiner

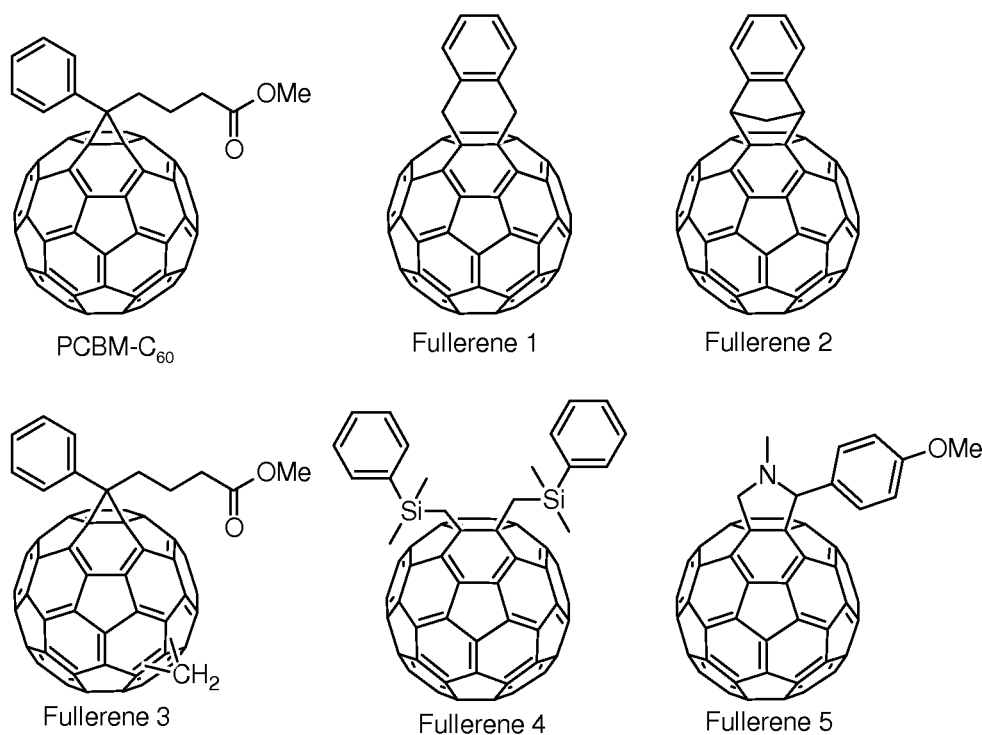

CYCLOHEXADIENE FULLERENE DERIVATIVES

TECHNICAL FIELD

The invention relates to novel fullerene derivatives, to methods for their preparation and educts or intermediates used therein, to mixtures and formulations containing them, to the use of the fullerene derivatives, mixtures and formulations as organic semiconductors in, or for the preparation of, organic electronic (OE) devices, especially organic photovoltaic (OPV) devices and organic photodetectors (OPD), and to OE, OPV and OPD devices comprising, or being prepared from, these fullerene derivatives, mixtures or formulations.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, sensors, memory elements and logic circuits to name just a few. The organic semiconducting materials are typically present in the electronic device in the form of a thin layer, for example of between 50 and 300 nm thickness.

The photosensitive layer in an OPV or OPD device is typically composed of at least two materials, a p-type semiconductor such as a polymer, an oligomer or a define molecular unit and a n-type semiconductor such as a fullerene derivative, graphene, a metal oxide, or quantum dots. In recent years, many p-type semiconductors, mainly polymers, have been prepared to enhance the performance of an OPV device. In comparison, the development of n-type semiconductor has been limited to only a few selected candidates.

BRIEF DESCRIPTION OF THE DRAWING

FIG. 1—Shows some fullerene derivatives.

Novel n-type semiconductors as promising alternative to PCBM-$C_{60}$ fullerene are limited. FIG. 1 shows some known fullerene derivatives, including Fullerene 1 and the respective multiple adducts both described in WO2008/018931 and WO2010/087655, Fullerene 2 and the respective multiple adducts both described in U.S. Pat. No. 8,217,260, Fullerene 3 described in JP 2012-094829, Fullerene 4 described in WO 2009/008323 and JP 2011-98906 and Fullerene 5 and the respective multiple adducts both described in JP 2011-181719. However, the physical properties of these fullerene derivatives, such as solubility, light stability, thermal stability are limiting their use in commercial applications.

Thus there is still a need for fullerene derivatives which are easy to synthesize, especially by methods suitable for mass production, show good structural organization and film-forming properties, exhibit good electronic properties, especially a high charge carrier mobility, a good processability, especially a high solubility in organic solvents, and high light and thermal stability.

It was an aim of the present invention to provide fullerene derivatives that provide one or more of the above-mentioned advantageous properties. Another aim of the invention was to extend the pool of n-type OSC materials available to the expert. Other aims of the present invention are immediately evident to the expert from the following detailed description.

The inventors of the present invention have found that one or more of the above aims can be achieved by providing cyclohexadiene fullerenes as disclosed and claimed hereinafter.

Surprisingly it was found that these cyclohexadiene fullerenes demonstrate one or more of the improved properties as described above, especially for use in OPV/OPD applications, compared to the fullerenes disclosed in prior art.

Substituted cyclohexadiene fullerenes have been proposed for medical applications, see for example S. Durdagi et al., *Bioorg. Med. Chem.* 2008, 16, 9957-9974 and Periya et al., *Tetrahedron Letters* 2004, 45, 8311-8313.

Substituted cyclohexadiene fullerenes have also been used for fundamental studies, see for example Liou et al., *J. Chem. Soc., Chem. Commun.* 1995, 1603-1604, An et al., *J. Org. Chem.* 1995, 60, 6353-6361, Cossu et al., *J. Org. Chem.* 1996, 61, 153-158, Hsiao et al., *J. Am. Chem. Soc.* 1998, 120, 12232-12236, Qian et al., *J. Am. Chem. Soc.* 2000, 122, 8333-8334, Inoue et al., *Synlett* 2000, 1178-1180, Iwamatsu et al., *Org. Lett.* 2002, 4, 1217-1220, and Vida et al., *Macromol. Rapid Commun.* 2007, 28, 1345-1349.

KR 1128833 B1 describes an organic/inorganic hybrid solar cell containing a fullerene derivative and a dye in an inorganic semiconductor, where the fullerene derivative, including one monosubstituted cyclohexadiene fullerene example, contains at least one of carboxylic acid group, anhydride group, phosphoric acid group, siloxane group, and sulfonic acid group. However, such groups have the drawback that they can act as charge traps in an OPV device configuration and liberate acidic protons ($H^+$) that are detrimental for the performance and lifetime of the OPV device.

Until now monosubstituted or polysubstituted cyclohexadiene fullerenes as disclosed and claimed hereinafter have not been suggested as potential candidates to replace PCBM type fullerenes in the photoactive layer of a OPV or OPD device, or for use as p-type or n-type semiconductor in an OFET or OLED device.

For example, the data reported for the cyclohexadiene fullerenes that are functionalized with unsubstituted thiophene rings as disclosed in Vida et al., *Macromol. Rapid Commun.* 2007, 28, 1345-1349, do not suggest that these fullerene derivatives could be interesting candidates for OPV/OPD application, because relevant information for such a use, like the electron mobility, energetic level (particularly LUMO level) and solid state morphology have not been reported.

SUMMARY

The invention relates to compounds of formula I, including isomers thereof,

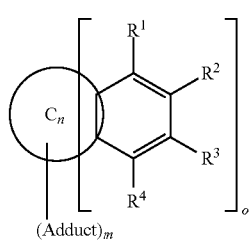

I wherein $C_n$ denotes a fullerene composed of n carbon atoms, optionally with one or more atoms trapped inside, Adduct is a secondary adduct, or a combination of secondary adducts, appended to the fullerene $C_n$ with any connectivity, m is 0, an integer $\geq 1$, or a non-integer $>0$, o is an integer $\geq 1$, $R^1$, $R^2$, $R^3$, $R^4$ independently of each other denote H, halogen, CN, $R^5$ or $R^6$, $R^5$ denotes a saturated or unsaturated, non-aromatic carbo- or heterocyclic group, or an aryl, heteroaryl, aryloxy or heteroaryloxy group, wherein each of the aforementioned groups has 3 to 20 ring atoms, is mono- or polycyclic, does optionally contain fused rings, and is optionally substituted by one or more halogen atoms or CN groups, or by one or more identical or different groups $R^6$, $R^6$ denotes an alkyl group with 1 to 30 C atoms, which is straight-chain, branched or cyclic, and in which one or more $CH_2$ groups are optionally replaced by —O—, —S—, —C(=O)—, —C(=S)—, —C(=O)—O—, —O—C(=O)—, —NR$^0$—, —C(=O)—NR$^0$—, —NR$^0$—C(=O)—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, $Y^1$ and $Y^2$ denote independently of each other H, F, Cl or CN, $R^0$ and $R^{00}$ denote independently of each other H or an optionally substituted carbyl or hydrocarbyl group having 1 to 40 C atoms, wherein at least one of $R^1$, $R^2$, $R^3$ and $R^4$ denotes $R^5$ that is substituted by one or more alkyl groups $R^6$ as defined above which have at least 3 C atoms and/or wherein at least one $CH_2$ group is replaced by —O—, —S—, —C(=O)—, —C(=S)—, —C(=O)—O—, —O—C(=O)—, —NR$^0$—, —SiR$^0$R$^{00}$—, —CF$_2$—, —CHR$^0$=CR$^{00}$—, —CY$^1$=CY$^2$— or —C≡C—.

The invention further relates to the use of compounds of formula I as electron acceptor or n-type semiconductor.

The invention further relates to the use of compounds of formula I as electron acceptor or n-type component in a semiconducting material, organic electronic device or component of an organic electronic device.

The invention further relates to a mixture comprising two or more fullerene derivatives, one or more of which are a compound of formula I.

The invention further relates to a mixture comprising one or more compounds of formula I, preferably as electron acceptor or n-type component, and further comprising one or more semiconducting compounds, which preferably have electron donor or p-type properties.

The invention further relates to a mixture comprising one or more compounds of formula I and one or more p-type organic semiconductor compounds, preferably selected from conjugated organic polymers.

The invention further relates to a mixture comprising one or more compounds of formula I and one or more compounds which are selected from compounds having one or more of a semiconducting, charge transport, hole transport, electron transport, hole blocking, electron blocking, electrically conducting, photoconducting and light emitting property.

The invention further relates to the use of a compound of formula I or a mixture comprising it as semiconducting, charge transport, electrically conducting, photoconducting, thermoelectric or light emitting material, or in an optical, electro-optical, electronic, electroluminescent, photoluminescent or thermoelectric device, or in a component of such a device or in an assembly comprising such a device or component.

The invention further relates to a semiconducting, charge transport, electrically conducting, photoconducting, thermoelectric or light emitting material, which comprises a compound of formula I or a mixture comprising it as described above and below.

The invention further relates to a formulation comprising one or more compounds of formula I, or a mixture or material comprising it as described above and below, and further comprising one or more solvents, preferably selected from organic solvents.

The invention further relates to an optical, electro-optical, electronic, electroluminescent, photoluminescent or thermoelectric device, or a component thereof, or an assembly comprising it, which is prepared using a formulation as described above and below.

The invention further relates to an optical, electro-optical, electronic, electroluminescent, photoluminescent or thermoelectric device, or a component thereof, or an assembly comprising it, which comprises a compound of formula I or a mixture or a material comprising it as described above and below.

The optical, electro-optical, electronic, electroluminescent, photoluminescent and thermoelectric devices include, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, laser diodes, Schottky diodes, photoconductors, photodetectors and thermoelectric devices.

The components of the above devices include, without limitation, charge injection layers, charge transport layers, interlayers, planarising layers, antistatic films, polymer electrolyte membranes (PEM), conducting substrates and conducting patterns.

The assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds, mixtures or materials of the present invention can be used as electrode materials in batteries and in components or devices for detecting and discriminating DNA sequences.

The invention further relates to a bulk heterojunction which comprises, or is being formed from, a mixture comprising one or more compounds of formula I and one or more p-type organic semiconductor compounds that are selected from conjugated organic polymers. The invention further relates to a bulk heterojunction (BHJ) OPV device or inverted BHJ OPV device, comprising such a bulk heterojunction.

Terms And Definitions

As used herein, the term "fullerene" will be understood to mean a compound composed of an even number of carbon atoms, which form a cage-like fused-ring having a surface which comprises six-membered rings and five-membered rings, usually with twelve five-membered rings and the rest six-membered rings, optionally with one or more atoms trapped inside. The surface of the fullerene may also contain hetero atoms like B or N.

As used herein, the term "endohedral fullerene" will be understood to mean a fullerene with one or more atoms trapped inside.

As used herein, the term "metallofullerene" will be understood to mean an endohedral fullerene wherein the atoms trapped inside are selected from metal atoms.

As used herein, the term "carbon based fullerene" will be understood to mean a fullerene without any atoms trapped inside, and wherein the surface is comprised only of carbon atoms.

As used herein, the term "polymer" will be understood to mean a molecule of relatively high molecular mass, the structure of which essentially comprises the multiple repetition of units derived, actually or conceptually, from molecules of relatively low molecular mass (*Pure Appl. Chem.*, 1996, 68, 2291). The term "oligomer" will be understood to mean a molecule of intermediate molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^5$ or $R^6$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as N, O, S, P, B, Si, Se, As, Te or Ge (for example carbonyl etc.). The term "hydrocarbyl group" will be understood to mean a carbyl group that does additionally contain one or more H atoms and optionally contains one or more hetero atoms like for example N, O, S, P, B, Si, Se, As, Te or Ge.

As used herein, the term "hetero atom" will be understood to mean an atom in an organic compound that is not a H- or C-atom, and preferably will be understood to mean N, O, S, P, B, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl groups include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched.

Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings and are optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, and is preferably alkyl, alkoxy, thioalkyl, alkylcarbonyl, alkoxycarbonyl or alkoxycarbonyloxy with 1 to 20 C atoms that is optionally fluorinated, and R$^0$, R$^{00}$, X$^0$ have the meanings given above and below.

Preferred substituents L are selected from halogen, most preferably F, or alkyl, alkoxy, oxaalkyl, thioalkyl, fluoroalkyl and fluoroalkoxy with 1 to 12 C atoms or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl or alkoxy group, i.e., where the terminal $CH_2$ group is replaced by —O—, can be straight-chain or branched. It is preferably straight-chain, has 2, 3, 4, 5, 6, 7, 8 or 12 carbon atoms and accordingly is preferably ethyl, propyl, butyl, pentyl, hexyl, heptyl, octyl or dodecyl, ethoxy, propoxy, butoxy, pentoxy, hexoxy, heptoxy, octoxy or dodecoxy furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one $CH_2$ group is replaced by —S—, is preferably straight-chain thiomethyl (—$SCH_3$), 1-thioethyl (—$SCH_2CH_3$), 1-thiopropyl (=-$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, in particular 1,1-difluoroalkyl, all of which are straight-chain or branched.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methylpentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the alkyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

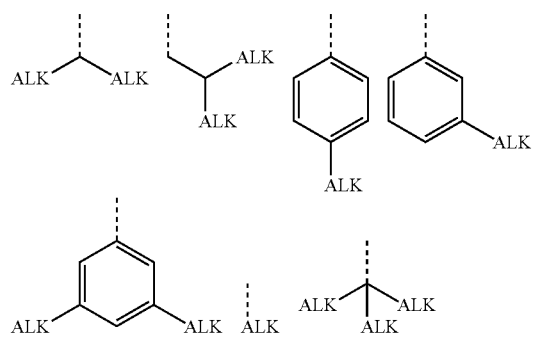

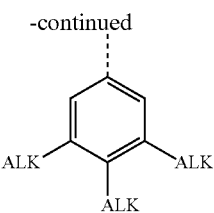

wherein "ALK" denotes optionally fluorinated and straight-chain or branched, preferably straight-chain, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

As used herein, "halogen" includes F, Cl, Br or I, preferably F, Cl or Br.

As used herein, —CO—, —C(=O)— and —C(O)— will be understood to mean a carbonyl group, i.e. a group having the structure

DETAILED DESCRIPTION

The compounds of formula I are easy to synthesize, especially by methods suitable for mass production, and exhibit advantageous properties. For example, they show good structural organization and film-forming properties, exhibit good electronic properties, especially high charge carrier mobility, a good processability, especially a high solubility in organic solvents, and high light and thermal stability The compounds of formula I are especially suitable as electron acceptor or n-type semiconductor, especially in semiconducting materials containing both donor and acceptor components, and for the preparation of a mixture of p-type and n-type semiconductors which are suitable for use in BHJ OPV devices.

For OPV and OPD application, the monosubstituted or polysubstituted cyclohexadiene fullerenes of formula I, or a mixture comprising two or more fullerene derivatives, one or more of which are selected from formula I, is blended with a further p-type semiconductor such as a polymer, an oligomer or a defined molecular unit to form the active layer in the OPV/OPD device (also referred to as "photoactive layer").

The OPV/OPD device is usually further composed of a first, transparent or semi-transparent electrode, typically provided on a transparent or semi-transparent substrate, on one side of the active layer and a second metallic or semi-transparent electrode on the other side of the active layer. Additional interfacial layer(s) acting as hole blocking layer, hole transporting layer, electron blocking layer and/or electron transporting layer, typically comprising a metal oxide (for example, $ZnO_x$, $TiO_x$, ZTO, $MoO_x$, $NiO_x$), a salt (for example: LiF, NaF), a conjugated polymer electrolyte (for example: PEDOT:PSS or PFN), a conjugated polymer (for example: PTAA) or an organic compound (for example: NPB, $Alq_3$, TPD), can be inserted between the active layer and an electrode.

The compounds of formula I demonstrate the following improved properties compared to previously disclosed fullerene derivatives for OPV/OPD application.

i) Electron accepting and/or donating unit(s) in position $R^1$ to $R^4$ reduce the fullerene band-gap and therefore the potential for improved light absorption.

ii) Additional fine-tuning of the electronic energies (HOMO/LUMO levels) by careful selection of electron accepting and/or donating unit(s) in position $R^1$ to $R^4$ increases the open circuit potential ($V_{oc}$).

iii) Additional fine-tuning of the electronic energies (HOMO/LUMO levels) by careful selection of electron accepting and/or donating unit(s) in position $R^1$ to $R^4$ reduces the energy loss in the electron transfer process between the fullerene derivative and a p-type material (for example a polymer, oligomer or defined molecular unit) when used in the active layer of an OPV or OPD device.

iv) Substituents $R^1$ to $R^4$ which can each possess more than one solubilising group enable higher fullerene solubility in non-halogenated solvents due to the increased number of solubilising groups.

v) Compared to the fullerene derivatives of the present invention, the fullerene derivatives reported in prior art, for example in Vida et al., *Macromol. Rapid Commun.* 2007, 28, 1345-1349, have very low solubility in solvents commonly used to prepare OPV devices.

vi) Vida et al. report that a cyclohexadiene fullerene functionalized with unsubstituted thiophene rings can be easy electropolymerised. This would lead to a significant drop in device performance, if the phenomenon would occur in the active layer of an OPV or OPD device. In the fullerene derivatives of the present invention the 2-position on the thiophene, ring is protected by a substituent to avoid such reaction in the device.

In the compounds of formula I and its subformulae, o preferably denotes 1, 2, 3 or, 4, very preferably 1 or 2.

In the compounds of formula I and its subformulae, the number of carbon atoms n of which the fullerene $C_n$ is composed is preferably 60, 70, 76, 78, 82, 84, 90, 94 or 96, very preferably 60 or 70.

The fullerene $C_n$ in formula I and its subformulae is preferably selected from carbon based fullerenes, endohedral fullerenes, or mixtures thereof, very preferably from carbon based fullerenes.

Suitable and preferred carbon based fullerenes include, without limitation, $(C_{60-Ih})$[5,6]fullerene, $(C_{70-D5h})$[5,6]fullerene, $(C_{76-D2})$[5,6]fullerene, $(C_{84-D2*})$[5,6]fullerene, $(C_{84-D2d})$[5,6]fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, $Sc_3N$@$C_{80}$, $Y_3N$@$C_{80}$, $Sc_3C_2$@$C_{80}$ or a mixture of two or more of the aforementioned metallofullerenes.

Preferably the fullerene $C_n$ is substituted at a [6,6] and/or [5,6] bond, preferably substituted on at least one [6,6] bond.

In addition to the benzene ring shown in formula I, the fullerene $C_n$ may have any number (m) of secondary adducts appended, named "Adduct" in formula I. The secondary adduct may be any possible adduct or combination of adducts with any connectivity to the fullerene.

In the compounds of formula I and its subformulae, all adducts may be connected to one another in any combination in the finished product or during synthesis, to facilitate preferred properties in the finished product.

In the compounds of formula I and its subformulae, the number m of secondary adducts appended to the fullerene $C_n$ is 0, an integer ≥1, or a non-integer >0 like 0.5 or 1.5, and is preferably 0, 1 or 2.

In a preferred embodiment the number m of the secondary adducts appended to the fullerene $C_n$ is 0.

In another preferred embodiment the number m of the secondary adducts appended to the fullerene $C_n$ is >0, preferably 1 or 2.

The secondary adduct, named "Adduct" in formula I and its subformulae, is preferably selected from the following formulae

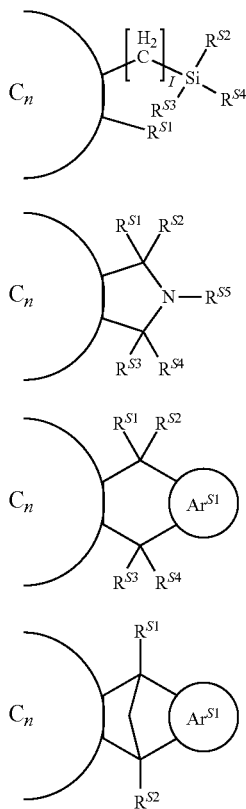
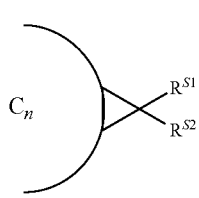
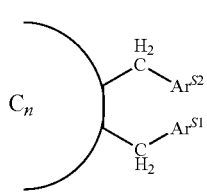

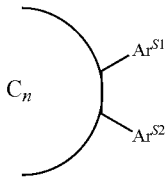
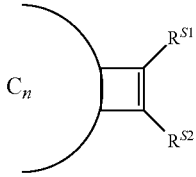
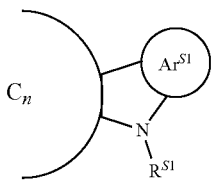
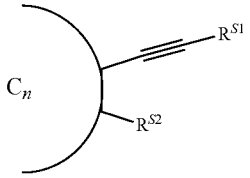
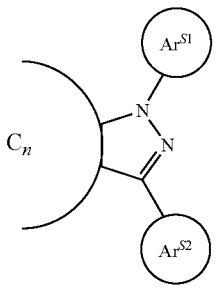

wherein
$R^{S1}$, $R^{S2}$, $R^{S3}$, $R^{S4}$ and $R^{S5}$ independently of each other denote H, halogen or CN, or have one of the meanings of $R^5$ or $R^6$ as given in formula I, and $Ar^{S1}$ and $Ar^{S2}$ are independently of each other an aryl or heteroaryl group with 5 to 20, preferably 5 to 15, ring atoms, which is mono- or polycyclic, and which is substituted by one or more identical or different substituents $R^S$, wherein $R^S$ denotes halogen, preferably F, or a straight-chain, branched or cyclic alkyl moiety with 1 to 30, preferably 4 to 20, very preferably 5 to 15, C atoms, in which one or more $CH_2$ groups are optionally replaced by —O—, —S—, —C(O)—, —C(S)—, —C(O)—O—, —O—C(O)—, —S(O)$_2$—, —NR$^0$—, —SiR$^0$R$^{00}$—, —CF$_2$—, wherein $R^0$ and $R^{00}$ have one of the meanings given above and below.

In the compounds of formula I and its subformulae, at least one of $R^1$, $R^2$, $R^3$ and $R^4$ denotes a cyclic group $R^5$ as defined in formula I, which is substituted by one or more alkyl groups $R^6$ as defined in formula I that have at least 3 C atoms and/or wherein at least one $CH_2$ group is replaced by —O—, —S—, —C(=O)—, —C(=S)—, —C(=O)—

—O—, —O—C(=O)—, —NR°—, —SiR°R°°—, —CF$_2$—, —CHR°=cR°°—, CY$^1$=CY$^2$— or —C≡C—.

Preferably R$^1$, R$^2$, R$^3$ and R$^4$ are independently of each other selected from H, halogen, CN, straight-chain, branched or cyclic alkyl with 1 to 30, preferably 4 to 20 C atoms, in which one or more CH$_2$ groups are optionally replaced by —O—, —S—, —C(O)—, —C(S)—, —C(O)—O—, —O—C(O)—, —NR°—, —SiR°R°°—, —CF$_2$—, or a carbocyclic or heterocyclic group selected from the following formulae

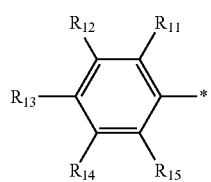
C-1

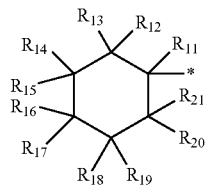
C-2

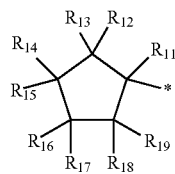
C-3

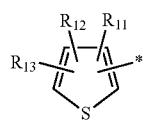
C-4

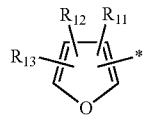
C-5

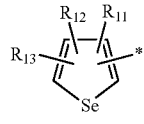
C-6

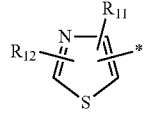
C-7

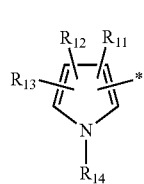
C-8

-continued

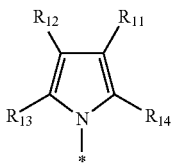
C-9

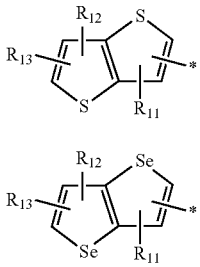
C-10

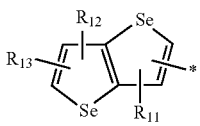
C-11

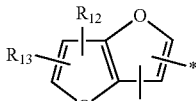
C-12

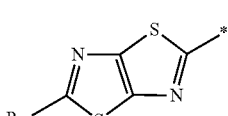
C-13

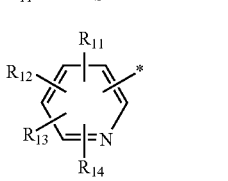
C-14

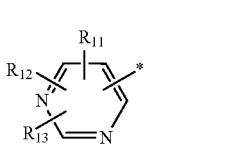
C-15

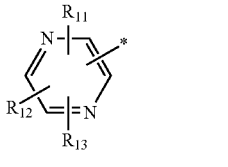
C-16

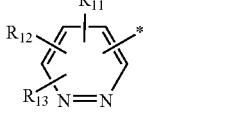
C-17

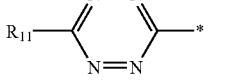
C-18

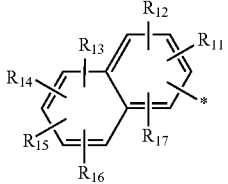
C-19

-continued

C-20, C-21, C-22, C-23, C-24

S-C-1, S-C-2, S-C-3, S-C-4, S-C-5, S-C-6, S-C-7, S-C-8, S-C-9, S-C-10 wherein $R^0$ and $R^{00}$ are as defined above and below, $R^{000}$ has one of the meanings of $R^{00}$ different from H, $R^{11}$, $R^{12}$, $R^{13}$, $R^{14}$, $R^{15}$, $R^{16}$, $R^{17}$ and $R^{18}$ independently of each other denote H, halogen or CN or have one of the meanings of $R^6$ or its preferred meanings as given above, and wherein in formula C-1 at least one of $R^{11}$, $R^{12}$, $R^{13}$, $R^{14}$ and $R^{15}$ is different from H and in formula C-4 at least one of $R^{11}$, $R^{12}$ and $R^{13}$ is different from H. Preferably in each of the aforementioned formulae at least one substituent $R^{11}$, $R^{12}$, $R^{13}$, $R^{14}$, $R^{15}$, $R^{16}$, $R^{17}$ or $R^{18}$ is different from H.

In formulae C-4, C-5, C-6 and C-7 the linkage to the cyclohexadiene fullerene is preferably located in 2-position (relative to the hetero atom), and the substituent $R^{13}$ in 5-position is preferably different from H.

In formulae C-10, C-11 and C-12 the linkage to the cyclohexadiene fullerene is preferably located in 2-position (relative to the hetero atom), and the substituent $R^{13}$ in 5-position is preferably different from H.

In formulae C-20, C-21 and C-22 the linkage to the cyclohexadiene fullerene is preferably located in 2-position (relative to the hetero atom).

Very preferably $R^1$, $R^2$, $R^3$ and $R^4$ are independently of each other selected from H, straight-chain branched or cyclic alkyl with 1 to 30, preferably 4 to 20, C atoms, —O—, —COOR$^{000}$, —COR$^{000}$, CONR$^0$R$^{000}$, —F—, —Cl, —NR$^0$R$^{000}$, or a carbocyclic or heterocyclic group selected from the following formulae wherein $R^0$ and $R^{00}$ are as defined above and below, $R^{000}$ has one of the meanings of $R^{00}$ different from H, $R^{11}$, $R^{12}$, $R^{13}$, $R^{14}$, $R^{15}$, $R^{16}$, $R^{17}$ and $R^{18}$, independently of each other denote H, halogen or CN or have one of the meanings of $R^6$ or its preferred meanings as given above, wherein in formulae S—C-1 and S—C-4 $R^{11}$ is different from H. Preferably in each of the aforementioned formulae at least one substituent $R^{11}$, $R^{12}$, $R^{13}$, $R^{14}$, $R^{15}$, $R^{16}$, $R^{17}$ or $R^{18}$ is different from H.

Preferably $R^6$ is straight-chain, branched or cyclic alkyl with 1 to 30, preferably 4 to 30, very preferably 4 to 20 C atoms, in which one or more $CH_2$ groups are optionally replaced by —O—, —S—, —C(O)—, —O(S)—, —C(O)—O—, —O—C(O)—, —$NR^0$—, —$SiR^0R^{00}$—, —$CF_2$—, and wherein one or more H atoms are replaced by fluorine atoms, wherein $R^0$ and $R^{00}$ have one of the meanings given above and below.

Further preferred groups $R^6$ are selected from alkyl, fluoroalkyl, alkoxy and thioalkyl having 1 to 30, preferably 4 to 30, very preferably 4 to 20, most preferably 5 to 15 C atoms.

$R^0$ and $R^{00}$ preferably denote, independently of each other, H or alkyl with 1 to 12 C-atoms. $R^{000}$ preferably denotes alkyl with 1 to 12 C atoms.

The compounds of formula I can be synthesized according to or in analogy to methods that are known to the skilled person and are described in the literature. Further synthesis methods can be taken from the examples.

For example, the cyclohexadiene fullerenes of formula I and its subformulae can be prepared by Danishefsky's diene cycloaddition, see for example J. Org. Chem. 1996, 60, 6353-6361, J. Am. Chem. Soc. 2000, 122, 8333-8334, ene-diyne cycloaddition, see for example, J. Am. Chem. Soc. 1998, 120, 12232-12236, [2+2+2] cycloaddition, see for example, J. Chem. Soc., Chem. Commun., 1995, 1603-1604, Synlett 2000, 1178-1180, and Diels-Alder reaction, see for example, Macromol. Rapid Commun. 2007, 28, 1345-1349, J. Org. Chem. 1996, 61, 153-158. Heterocycle substituted cyclohexadiene fullerenes have only been demonstrated using Diels-Alder reaction in Macromol. Rapid Commun. 2007, 28, 1345-1349.

Especially suitable and preferred synthesis methods of the compounds of formula I and its subformulae are illustrated in the synthesis schemes shown hereinafter, wherein $R^1$, $R^2$, $R^3$, $R^4$, $R^{11}$, $R^{12}$, $R^{13}$ and n are as defined above.

A suitable and preferred method for the general synthesis of a carbo- and heterocycle substituted cyclohexadiene fullerene is exemplarily illustrated in Scheme 1 below. A thiophene S,S-dioxide precursor is prepared with the desirable substitution in $R^1$ to $R^4$ and then is reacted with a fullerene source to provide a desirable fullerene derivative via Diels-Alder reaction.

Scheme 1
Generic synthesis of mono- (n = 1) or polysubstituted (n > 1) cyclohexadiene fullerene.

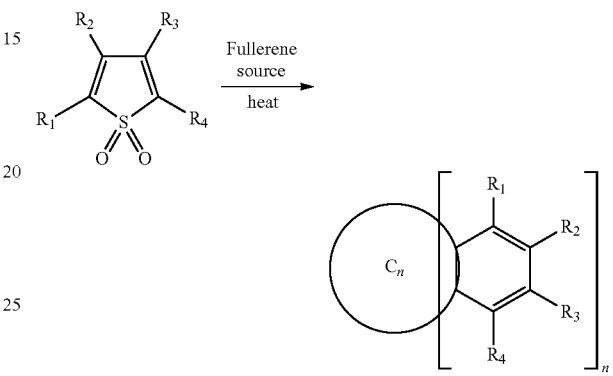

Specific fullerene derivatives of formula I or its subformulae can for example be prepared following the synthesis exemplarily illustrated in Scheme 2 below. Therein, 2,5-Diiodo-thiophene S,S-dioxide is reacted in a cross coupling reaction with the desirable carbo- or heterocycles ring to form a substituted precursor. Alternatively the precursor can also be prepared following the synthesis exemplarily illustrated in Scheme 3 below. Therein, the 2,5-disubstituted thiophene is prepared from cross coupling reaction with the desirable carbo- or heterocycles ring and oxidised to form a substituted precursor. This precursor is then reacted with a fullerene source to provide a desirable fullerene derivative via Diels-Alder reaction.

Scheme 2
Synthesis of a monosubstituted cyclohexadiene fullerene.

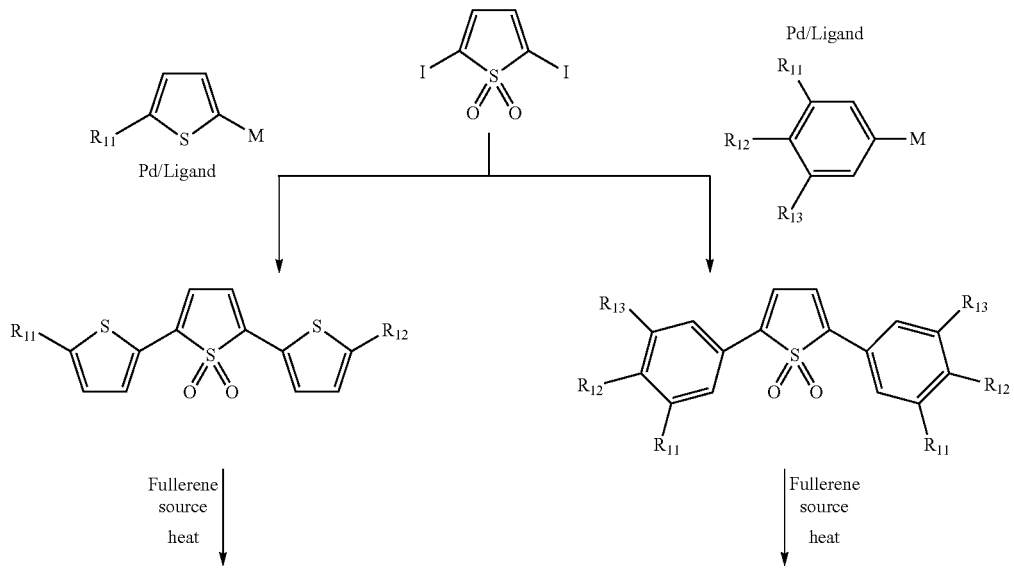

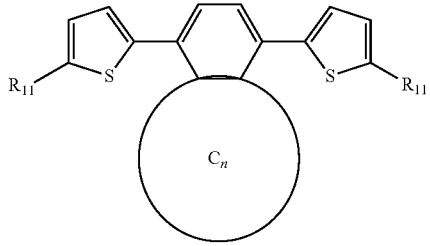
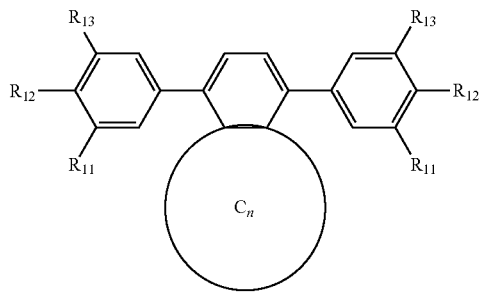

A preferred embodiment of the present invention relates to a fullerene mixture, comprising one or more fullerene derivatives, at least one of which is a fullerene derivative of this invention, and further comprising one or more conjugated organic polymers, which are preferably selected from electron donor, or p-type, semiconducting polymers.

Such a fullerene mixture is especially suitable for use in the photoactive layer of an OPV or OPD device. Preferably the fullerene(s) and polymer(s) are selected such that the fullerene mixture forms a bulk heterojunction (BHJ).

A suitable conjugated organic polymer (hereinafter simply referred to as "polymer") for use in a fullerene mixture according to the present invention can be selected from polymers as described in prior art, for example in WO/2010/008672, WO/2010/049323, WO 2011/131280, WO/2011/052709, WO/2011/052710, US/2011/0017956, WO/2012/030942 or US/8334456B2.

A preferred polymer is selected from the group consisting of poly(3-substituted thiophene) and poly(3-substituted selenophene), for example poly(3-alkyl thiophene) or poly(3-alkyl selenophene), preferably poly(3-hexyl thiophene) or poly(3-hexyl selenophene).

A further preferred polymer comprises one or more repeating units selected from formulae IIa and IIb:

$$-[(Ar^1)_a\text{-}(D)_b\text{-}(Ar^2)_c\text{-}(Ar^3)_d]- \qquad \text{IIa}$$

$$-[(Ar^1)_a\text{-}(A)_b\text{-}(Ar^2)_c\text{-}(Ar^3)_d]- \qquad \text{IIb}$$

wherein

A is arylene or heteroarylene with 5 to 30 ring atoms that is optionally substituted by one or more groups $R^S$, and preferably has electron acceptor property, D is arylene or heteroarylene with 5 to 30 ring atoms that is different from A, is optionally substituted by one or more groups $R^S$, and preferably has electron donor property, $Ar^1$, $Ar^2$, $Ar^3$ are, on each occurrence identically or differently, and independently of each other, arylene or heteroarylene that is different from A and D, preferably has 5 to 30 ring atoms, and is optionally substituted, preferably by one or more groups $R^S$, $R^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, $R^0$ and $R^{00}$ are independently of each other H or optionally substituted $C_{1-40}$ carbyl or hydrocarbyl, and preferably denote H or alkyl with 1 to 12 C-atoms, $X^0$ is halogen, preferably F, Cl or Br,

Scheme 3
Alternative synthesis of a monosubstituted cyclohexadiene fullerene.

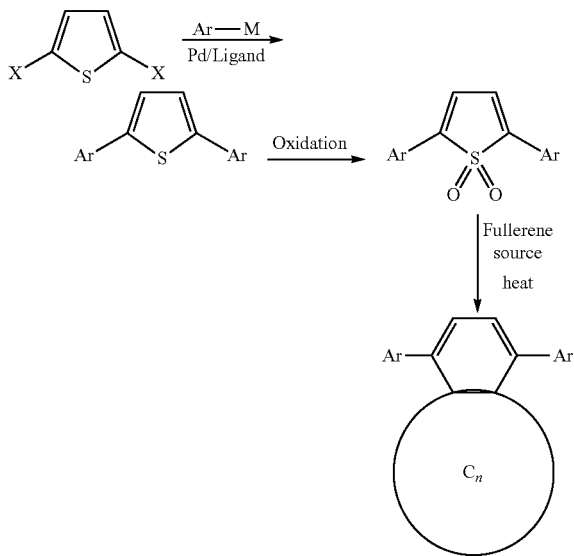

The novel methods of preparing fullerene derivatives as described above and below, and the intermediates used therein, are another aspect of the invention.

The compounds of formula I or its subformulae can also be used in mixtures, for example together with other monomeric compounds, or polymers, having one or more of a semiconducting, charge transport, hole transport, electron transport, hole blocking, electron blocking, electrically conducting, photoconducting and light emitting property Thus, another aspect of the invention relates to a mixture (hereinafter referred to as "fullerene mixture"), comprising one or more fullerene derivatives of formula I or its subformulae or of a preferred embodiment as described above and below (hereinafter simply referred to as "fullerene derivative of this invention"), and one or more additional compounds, preferably having one or more of a semiconducting, charge transport, hole transport, electron transport, hole blocking, electron blocking, electrically conducting, photoconducting and light emitting property.

The additional compounds in the fullerene mixture can be selected for example from fullerene derivatives other than those of this invention, or from conjugated organic polymers.

The fullerene mixture can be prepared by conventional methods that are described in prior art and known to the skilled person.

a, b, c are on each occurrence identically or differently 0, 1 or 2, d is on each occurrence identically or differently 0 or an integer from 1 to 10.

Preferably the polymer comprises at least one repeating unit of formula IIa wherein b is at least 1. Further preferably the polymer comprises at least one repeating unit of formula IIa wherein b is at least 1, and at least one repeating unit of formula IIb wherein b is at least 1.

A further preferred polymer comprises, in addition to the units of formula IIa and/or IIb, one or more repeating units selected from monocyclic or polycyclic arylene or heteroarylene groups that are optionally substituted.

These additional repeating units are preferably selected of formula III

—[(Ar$^1$)$_a$—(Ar$^2$)$_c$—(Ar$^3$)$_d$]—   III wherein Ar$^1$, Ar$^2$, Ar$^3$, a, c and d are as defined in formula IIa.

R$^S$ preferably denotes, on each occurrence identically or differently, H, straight-chain, branched or cyclic alkyl with 1 to 30 C atoms, in which one or more CH$_2$ groups are optionally replaced by —O—, —S—, —C(O)—, —C(S)—, —C(O)—O—, —O—C(O)—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, or denotes aryl, heteroaryl, aryloxy or heteroaryloxy with 4 to 20 ring atoms which is optionally substituted, preferably by halogen or by one or more of the aforementioned alkyl or cyclic alkyl groups.

Further preferably the polymer is selected of formula IV:

*—[—(A)$_x$-(B)$_y$-(C)$_z$—]$_n$—*   IV wherein
A, B, C independently of each other denote a distinct unit of formula IIa, IIb or III,
x is >0 and ≤1,
y is ≥0 and <1,
z is ≥0 and <1,
x+y+z is 1, and
n is an integer >1.

Preferably at least one of B or C denotes a unit of formula IIa. Very preferably one of B and C denotes a unit of formula IIa and one of B and C denotes a unit of formula IIb.

A preferred polymer of formula IV is selected from the following formulae

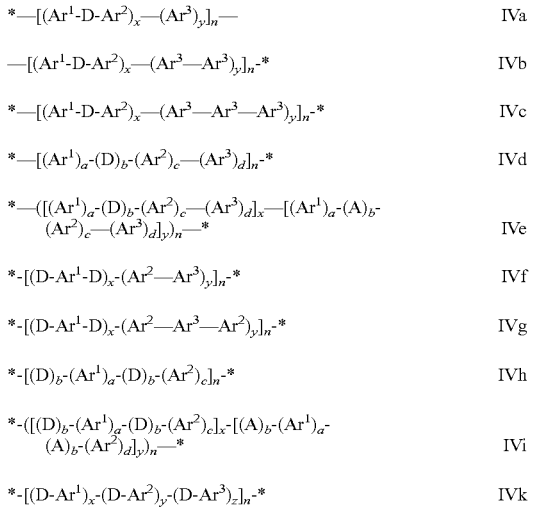

*—[(Ar$^1$-D-Ar$^2$)$_x$—(Ar$^3$)$_y$]$_n$—   IVa

—[(Ar$^1$-D-Ar$^2$)$_x$—(Ar$^3$—Ar$^3$)$_y$]$_n$-*   IVb

*—[(Ar$^1$-D-Ar$^2$)$_x$—(Ar$^3$—Ar$^3$—Ar$^3$)$_y$]$_n$-*   IVc

*—[(Ar$^1$)$_a$-(D)$_b$-(Ar$^2$)$_c$—(Ar$^3$)$_d$]$_n$-*   IVd

*—([(Ar$^1$)$_a$-(D)$_b$-(Ar$^2$)$_c$—(Ar$^3$)$_d$]$_x$—[(Ar$^1$)$_a$-(A)$_b$-(Ar$^2$)$_c$—(Ar$^3$)$_d$]$_y$)$_n$—*   IVe

*-[(D-Ar$^1$-D)$_x$-(Ar$^2$—Ar$^3$)$_y$]$_n$-*   IVf

*-[(D-Ar$^1$-D)$_x$-(Ar$^2$—Ar$^3$—Ar$^2$)$_y$]$_n$-*   IVg

*-[(D)$_b$-(Ar$^1$)$_a$-(D)$_b$-(Ar$^2$)$_c$]$_n$-*   IVh

*-([(D)$_b$-(Ar$^1$)$_a$-(D)$_b$-(Ar$^2$)$_c$]$_x$-[(A)$_b$-(Ar$^1$)$_a$-(A)$_b$-(Ar$^2$)$_d$]$_y$)$_n$—*   IVi

*-[(D-Ar$^1$)$_x$-(D-Ar$^2$)$_y$-(D-Ar$^3$)$_z$]$_n$-*   IVk wherein D, Ar$^1$, Ar$^2$, Ar$^3$, a, b, c and d have in each occurrence identically or differently one of the meanings given in formula IIa, A has on each occurrence identically or differently one of the meanings given in formula IIb, and x, y, z and n are as defined in formula IV, wherein polymers can be alternating or random copolymers, and wherein in formula IVd and IVe in at least one of the repeating units [(Ar$^1$)$_a$-(D)$_b$-(Ar$^2$)$_c$—(Ar$^3$)$_d$] and in at least one of the repeating units [(Ar$^1$)$_a$-(A)$_b$-(Ar$^2$)$_c$—(Ar$^3$)$_d$] b is at least 1 and wherein in formula IVh and IVi in at least one of the repeating units [(D)$_b$-(Ar$^1$)$_a$-(D)$_b$-(Ar$^2$)$_d$] and in at least one of the repeating units [(D)$_b$-(Ar$^1$)$_a$-(D)$_b$-(Ar$^2$)$_d$] b is at least 1.

In the polymer, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The polymer can be a homopolymer or copolymer, like a statistical or random copolymer, alternating copolymer or block copolymer, or a combination of the aforementioned.

Especially preferred is a polymer selected from the following groups:

Group A consisting of homopolymers of the unit D or (Ar$^1$-D) or (Ar$^1$-D-Ar$^2$) or (Ar$^1$-D-Ar$^3$) or (D-Ar$^2$—Ar$^3$) or (Ar$^1$-D-Ar$^2$—Ar$^3$) or (D-Ar$^1$-D), i.e. where all repeating units are identical, Group B consisting of random or alternating copolymers formed by identical units (Ar$^1$-D-Ar$^2$) or (D-Ar$^1$-D) and identical units (Ar$^3$), Group C consisting of random or alternating copolymers formed by identical units (Ar$^1$-D-Ar$^2$) or (D-Ar$^1$-D) and identical units (A$^1$), Group D consisting of random or alternating copolymers formed by identical units (Ar$^1$-D-Ar$^2$) or (D-Ar$^1$-D) and identical units (Ar$^1$-A$^c$-Ar$^2$) or (A$^c$-Ar$^1$-A$^c$), wherein in all these groups D, A, Ar$^1$, Ar$^2$ and Ar$^3$ are as defined above and below, in groups A, B and C Ar$^1$, Ar$^2$ and Ar$^3$ are different from a single bond, and in group D one of Ar$^1$ and Ar$^2$ may also denote a single bond.

A preferred polymer of formula IV and IVa to IVk is selected of formula V

R$^{21}$-chain-R$^{22}$   V wherein "chain" denotes a polymer chain of formulae IV or IVa to IVk, and R$^{21}$ and R$^{22}$ have independently of each other one of the meanings of R$^S$ as defined above, or denote, independently of each other, H, F, Br, Cl, I, —CH$_2$Cl, —CHO, —CR'=CR''$_2$, —SiR'R''R''', —SiR'X'X'', —SiR'R''X', —SnR'R''R''', —BR'R'', —B(OR')(OR''), —B(OH)$_2$, —O—SO$_2$—R', —C≡CH, —C≡C—SiR'$_3$, —ZnX' or an endcap group, X' and X'' denote halogen, R', R'' and R''' have independently of each other one of the meanings of R$^0$ given in formula I, and two of R', R'' and R''' may also form a ring together with the hetero atom to which they are attached.

Preferred endcap groups R$^{21}$ and R$^{22}$ are H, C$_{1-20}$ alkyl, or optionally substituted C$_{6-12}$ aryl or C$_{2-10}$ heteroaryl, very preferably H or phenyl.

In the polymer represented by formula IV, IVa to IVk or V, x, y and z denote the mole fraction of units A, B and C, respectively, and n denotes the degree of polymerisation or total number of units A, B and C. These formulae includes block copolymers, random or statistical copolymers and alternating copolymers of A, B and C, as well as homopolymers of A for the case when x>0 and y=z=0.

Preferably D, Ar¹, Ar² and Ar³ are selected from the group consisting of the following formulae
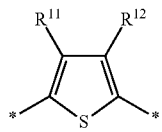 (D1)
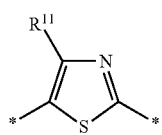 (D2)
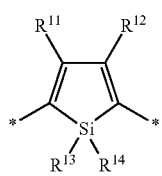 (D3)
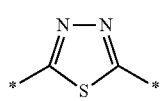 (D4)
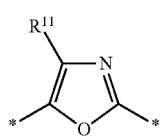 (D5)
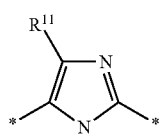 (D6)
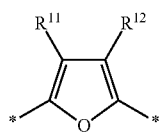 (D7)
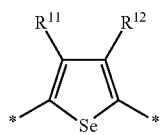 (D8)
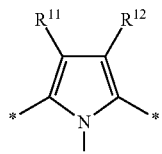 (D9)
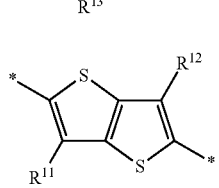 (D10)
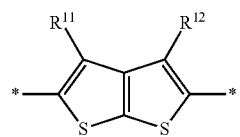 (D11)
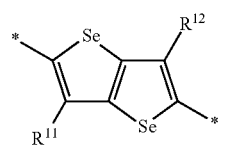 (D12)
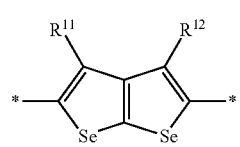 (D13)
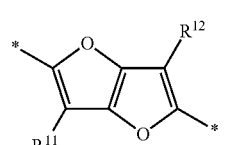 (D14)
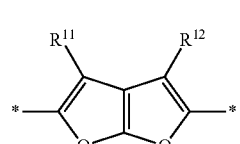 (D15)
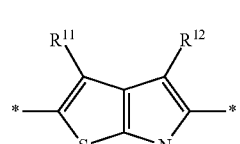 (D16)
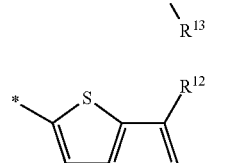 (D17)
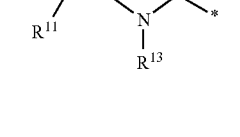 (D18)
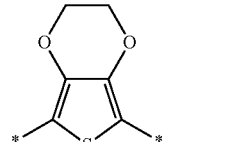 (D19)
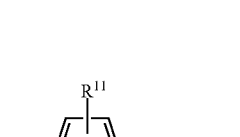

-continued
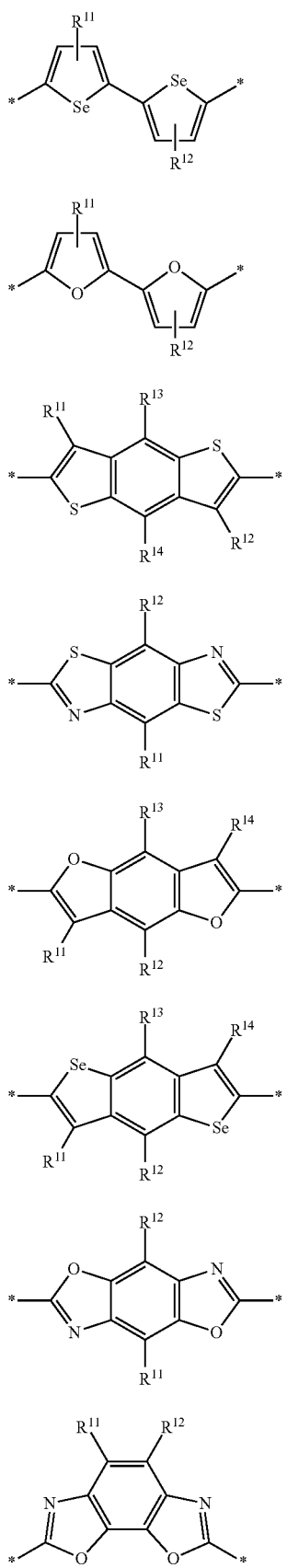
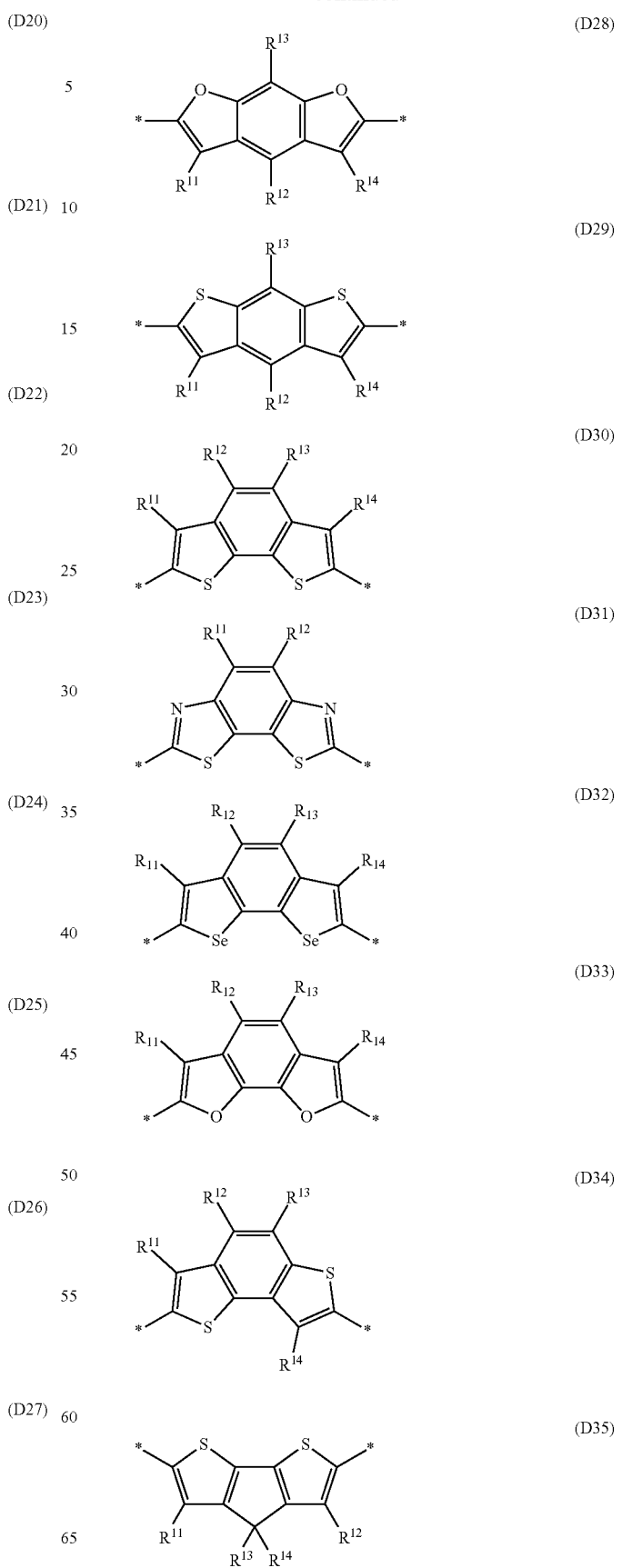

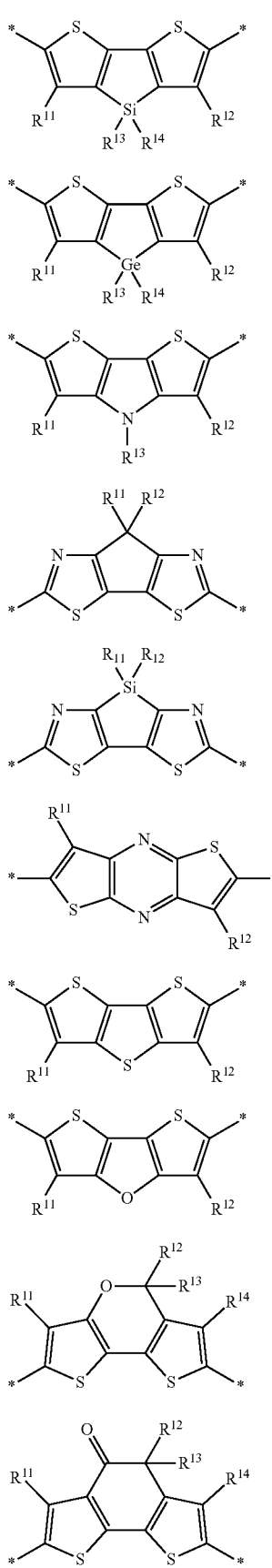
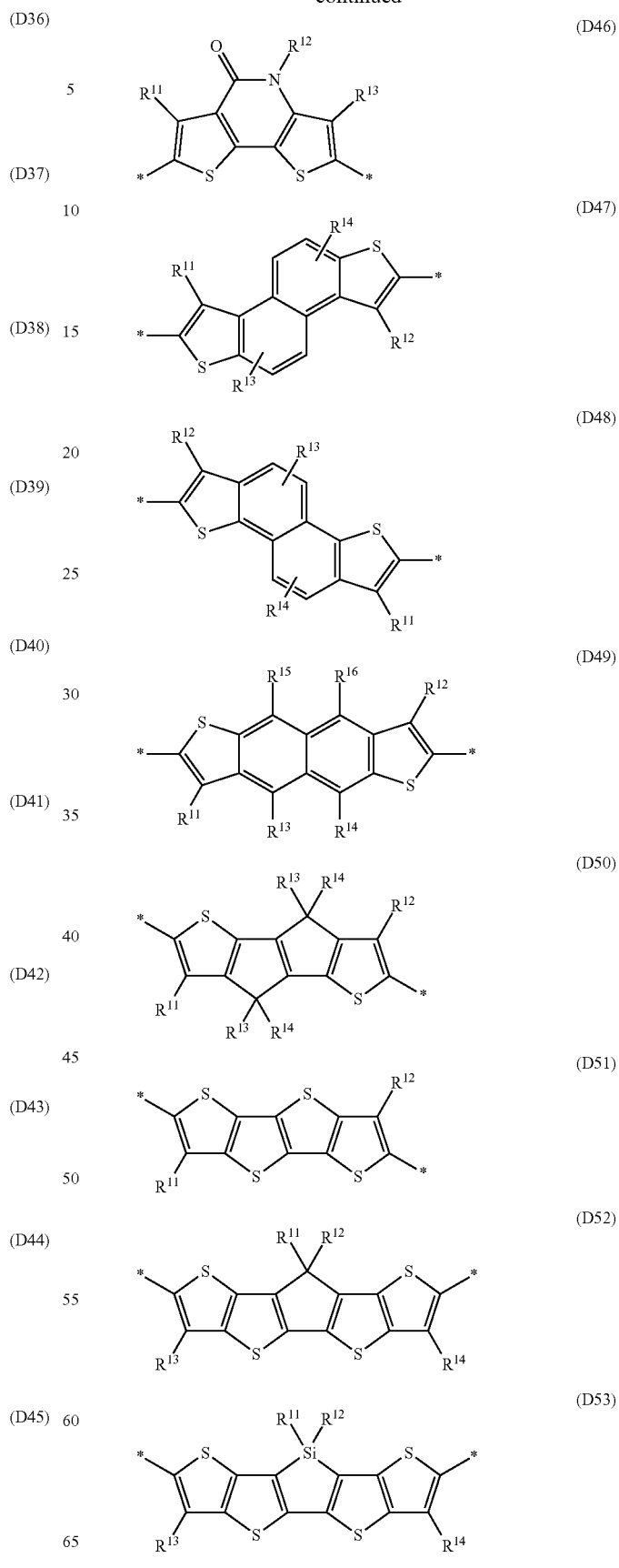

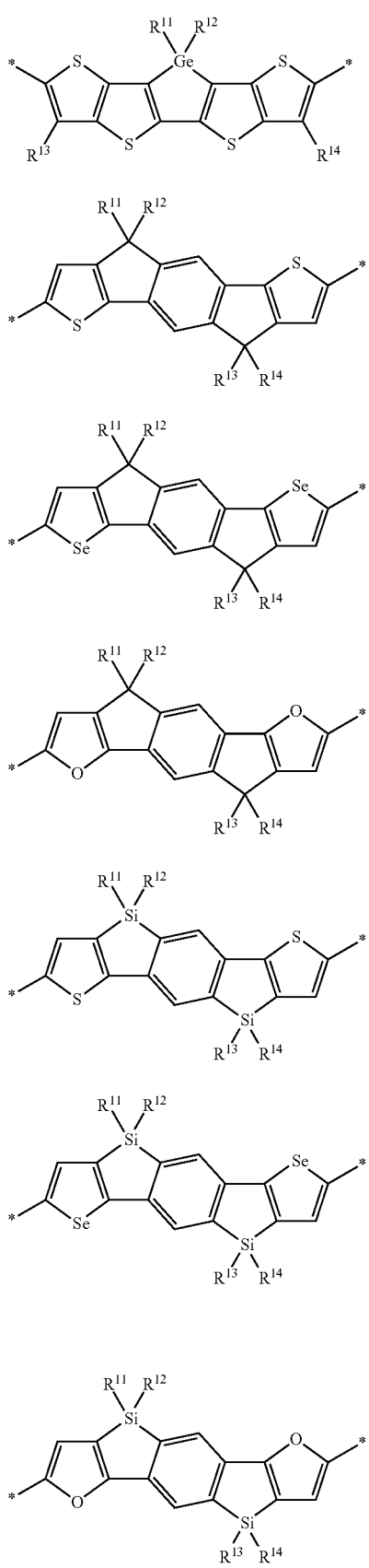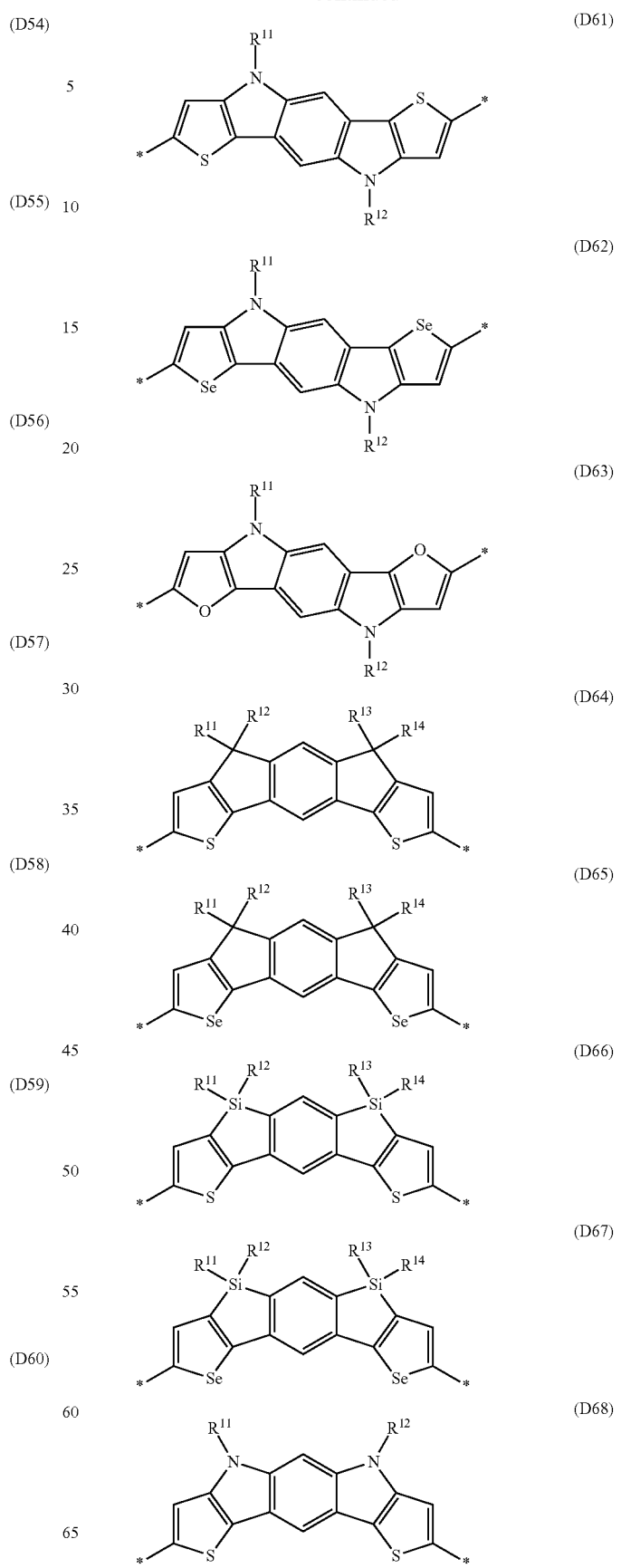

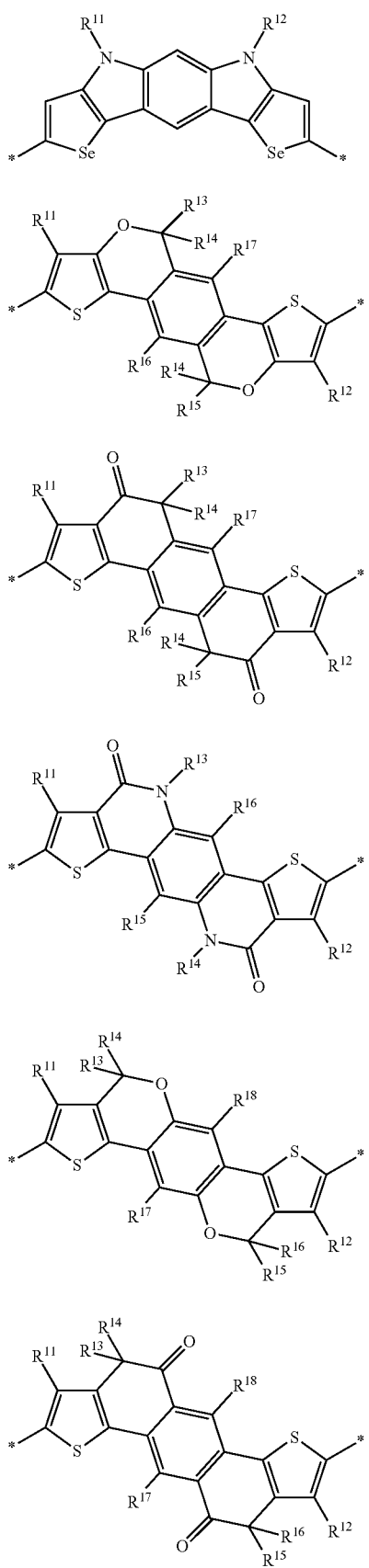
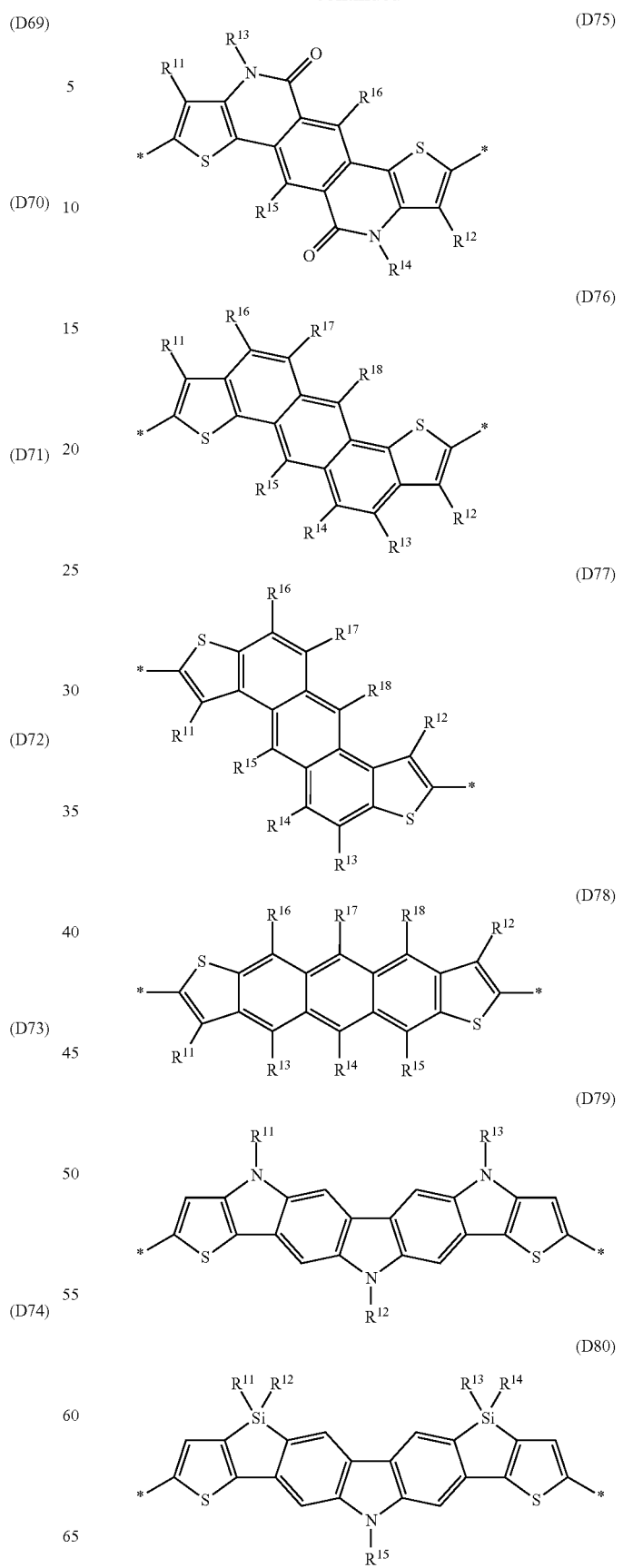

-continued
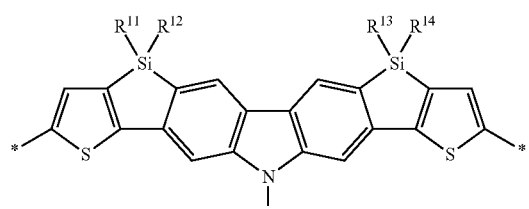
(D81)
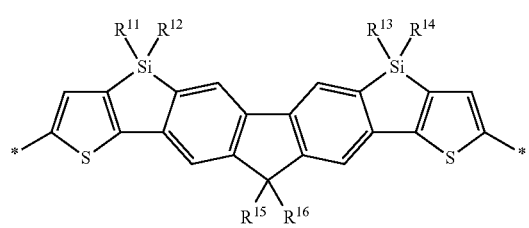
(D82)
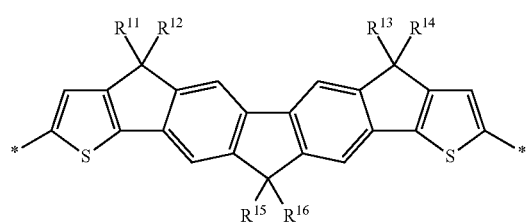
(D83)
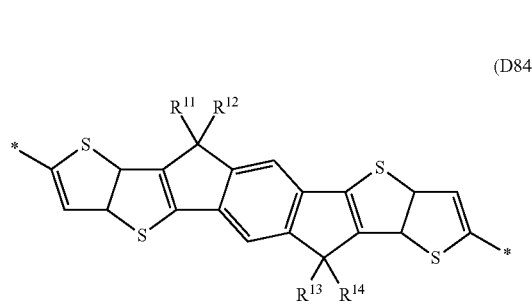
(D84)
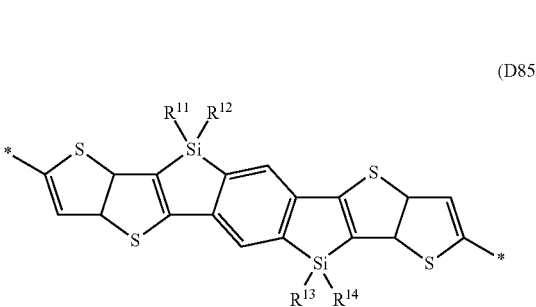
(D85)
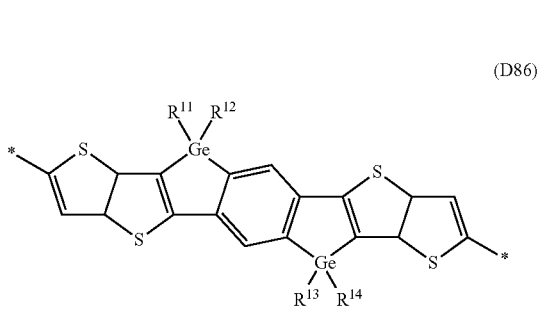
(D86)
-continued
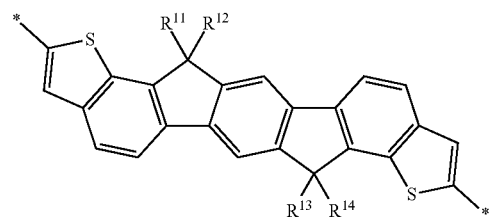
(D87)
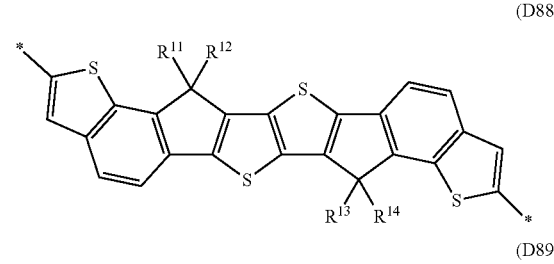
(D88)
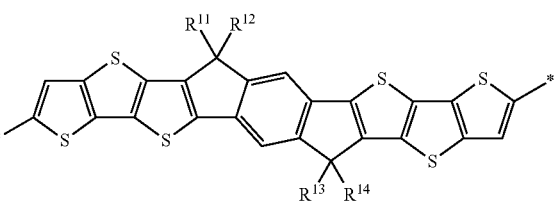
(D89)
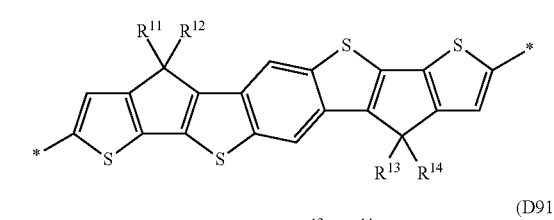
(D90)
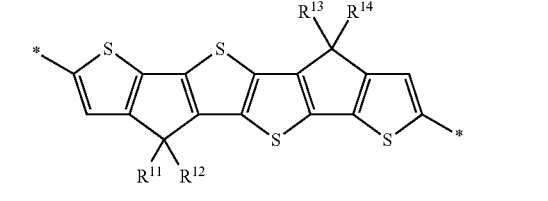
(D91)
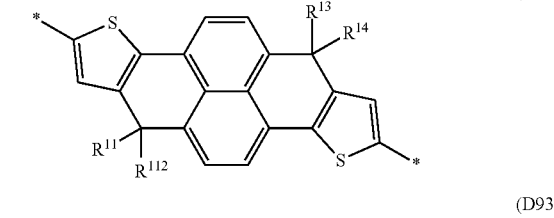
(D92)
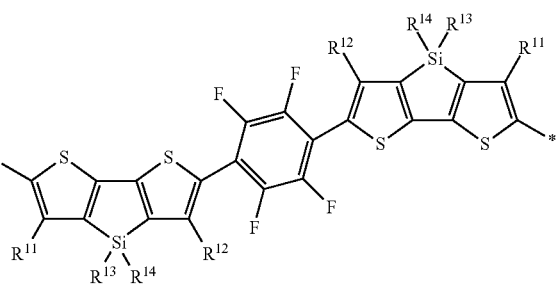
(D93)

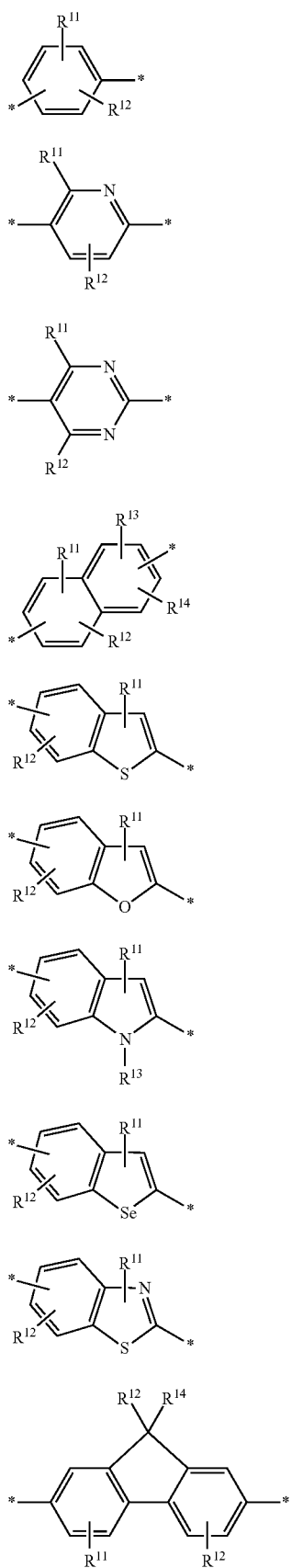
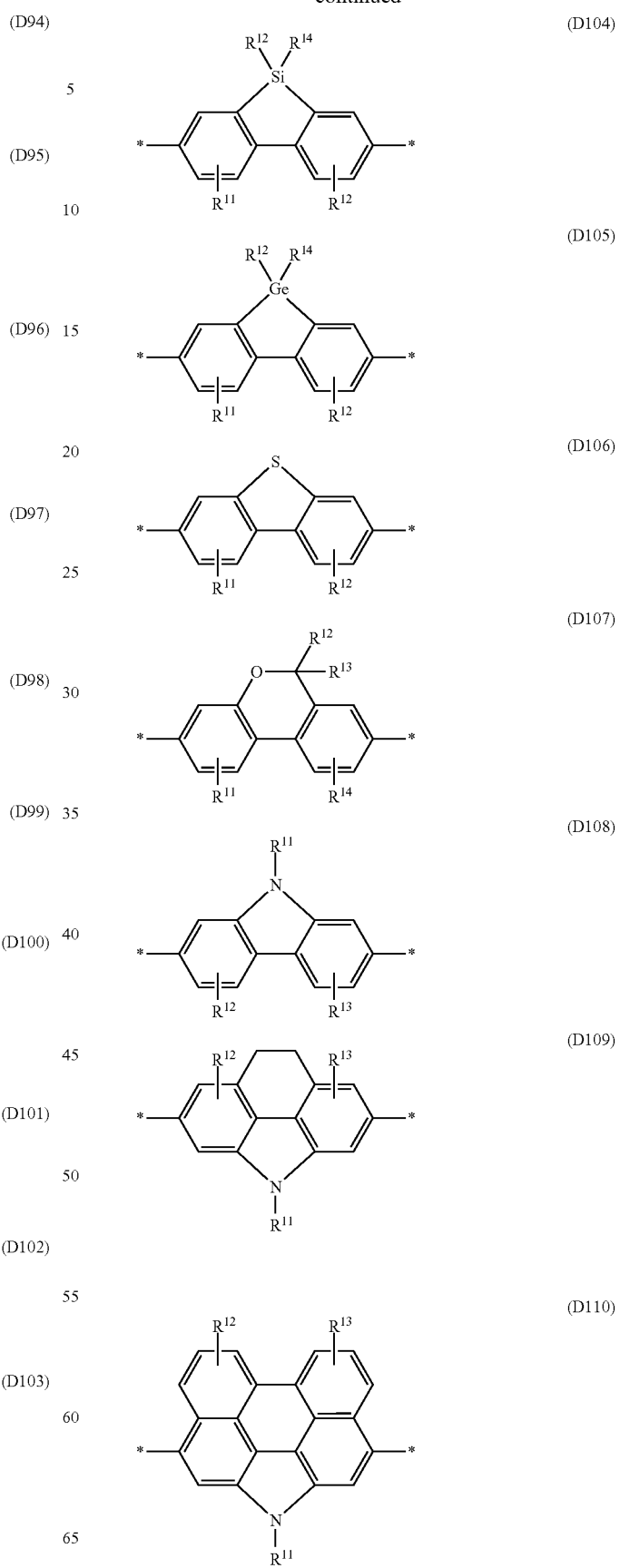

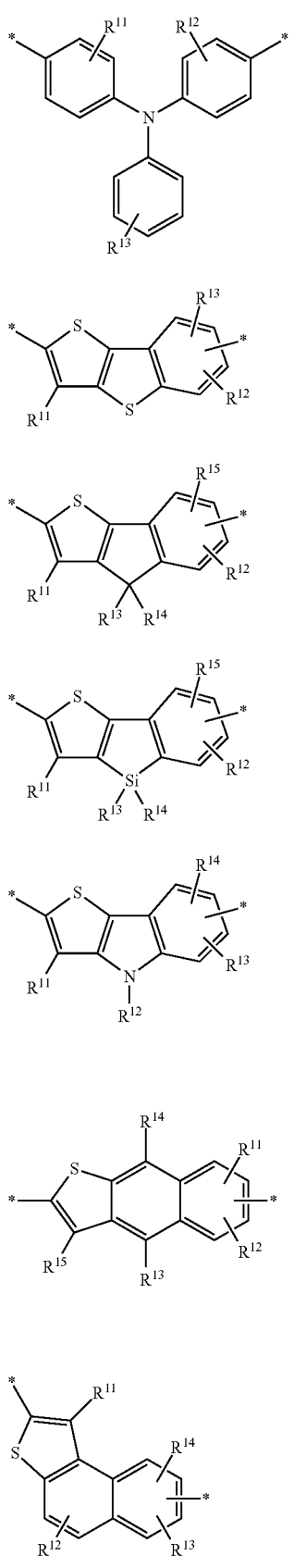
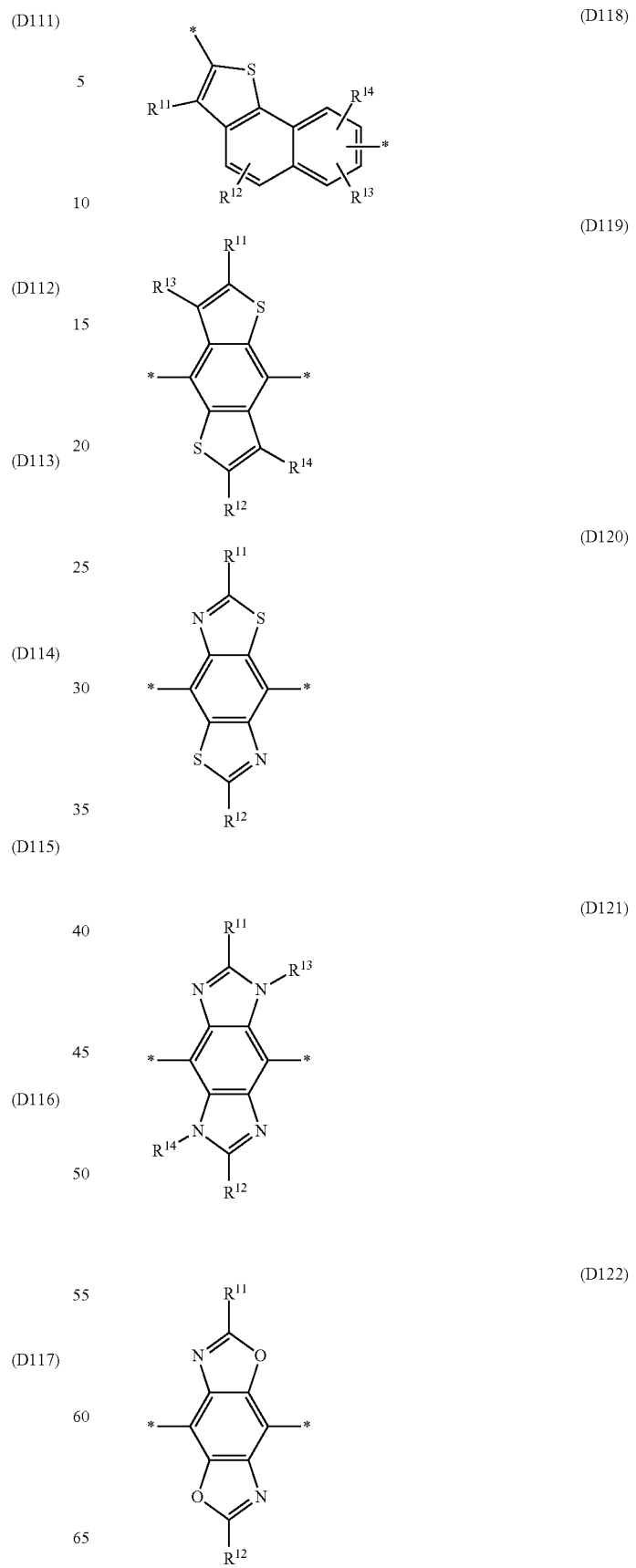

-continued
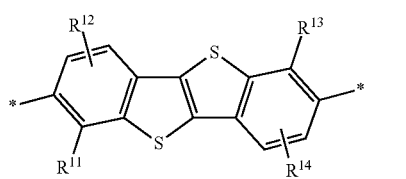
(D123)
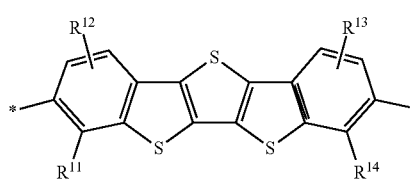
(D124)
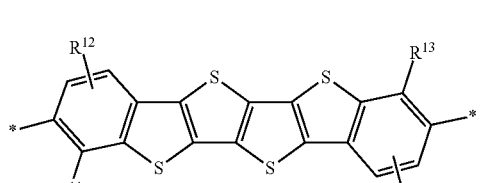
(D125)
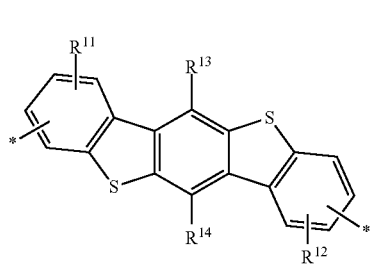
(D126)
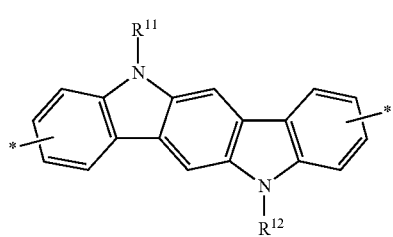
(D127)
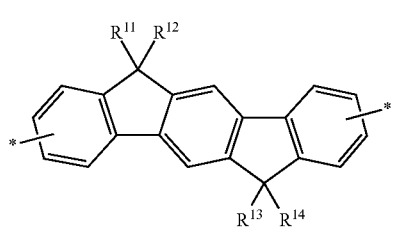
(D128)
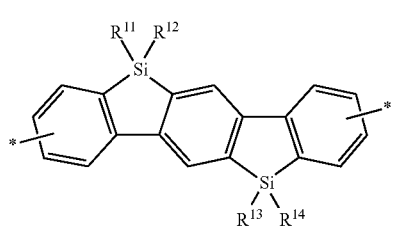
(D129)
-continued
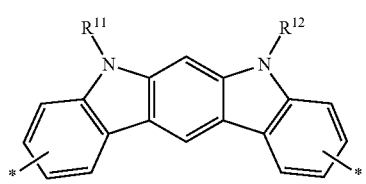
(D130)
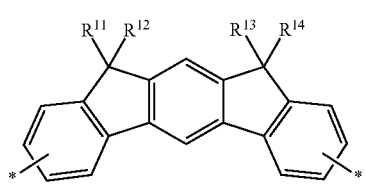
(D131)
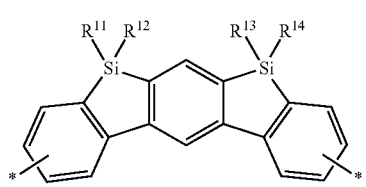
(D132)
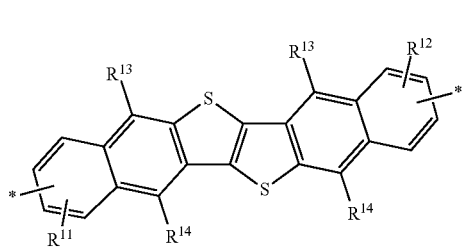
(D133)
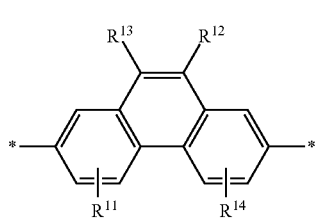
(D134)
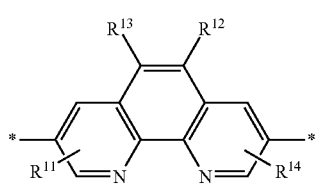
(D135)
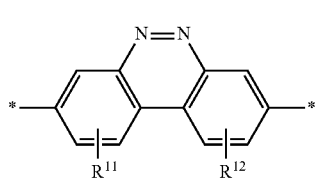
(D136)
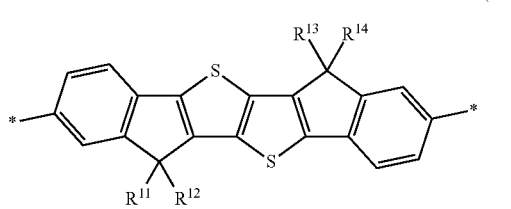
(D137)

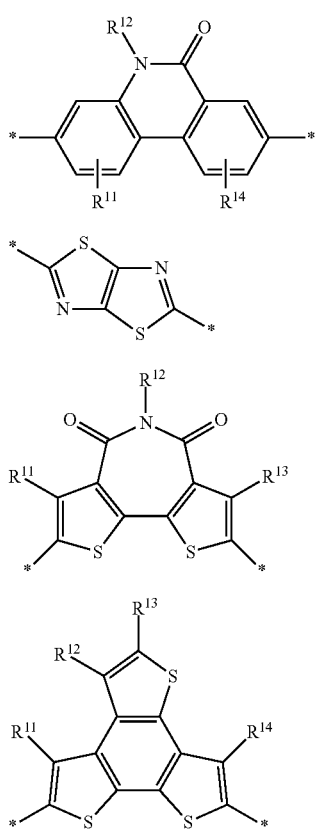
(D138)
(D139)
(D140)
(D141)
wherein $R^{11}$, $R^{12}$, $R^{13}$, $R^{14}$, $R^{15}$, $R^{16}$, $R^{17}$ and $R^{18}$ independently of each other denote H or have one of the meanings of $R^S$ as defined above and below.
Further preferably A, $Ar^1$, $Ar^2$ and $Ar^3$ are selected from the group consisting of the following formulae
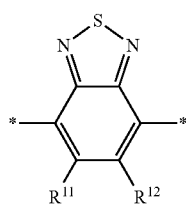
(A1)
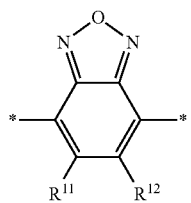
(A2)
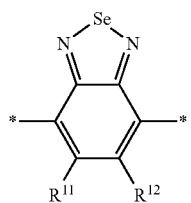
(A3)
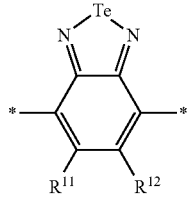
(A4)
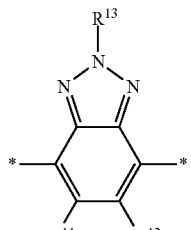
(A5)
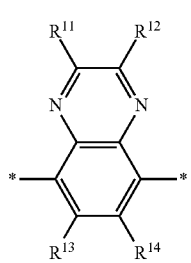
(A6)
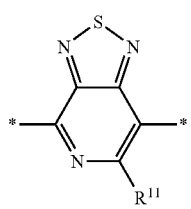
(A7)
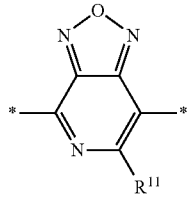
(A8)
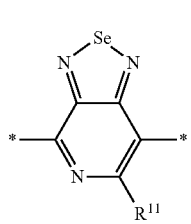
(A9)
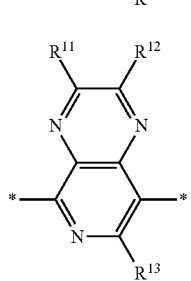
(A10)

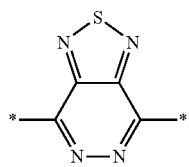 (A11)
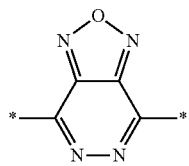 (A12)
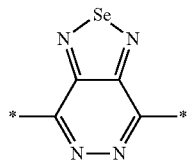 (A13)
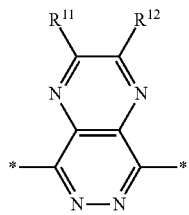 (A14)
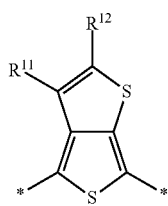 (A15)
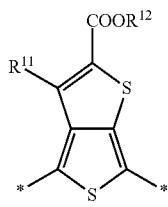 (A16)
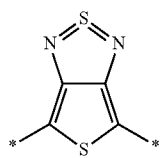 (A17)
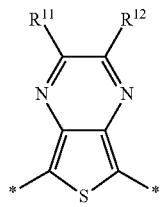 (A18)
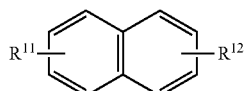 (A19)
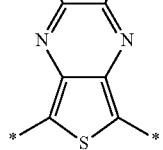 (A20)
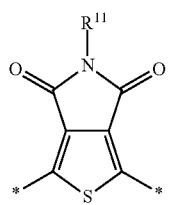 (A21)
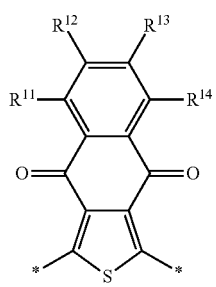 (A22)
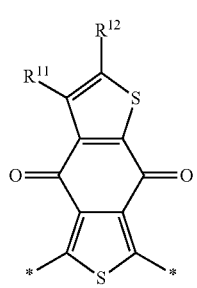 (A23)
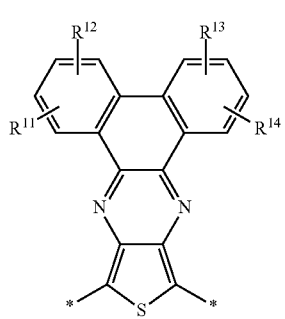

-continued
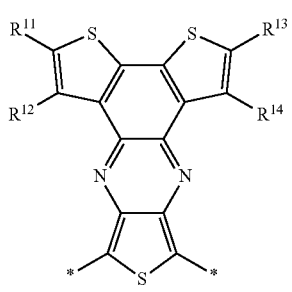
(A24)
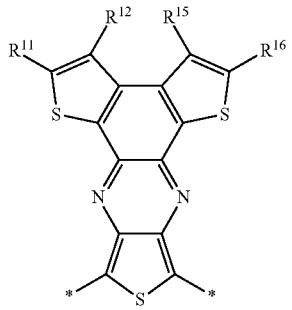
(A25)
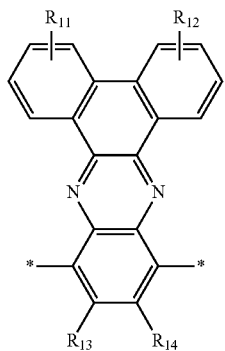
(A26)
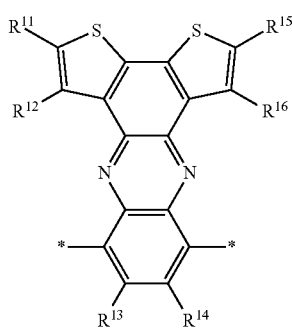
(A27)
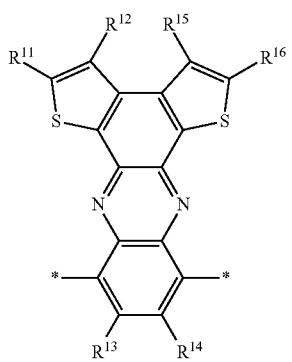
(A28)
-continued
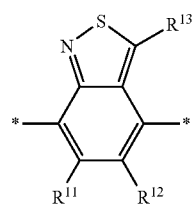
(A29)
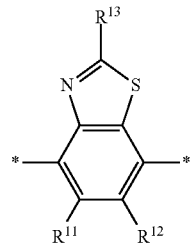
(A30)
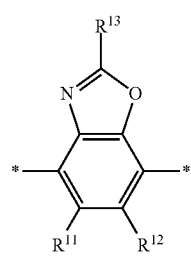
(A31)
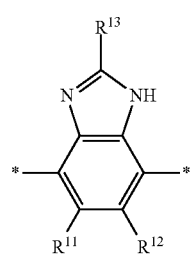
(A32)
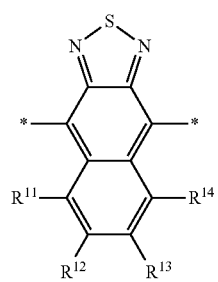
(A33)
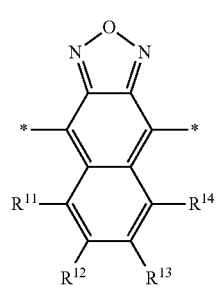
(A34)

(A35) 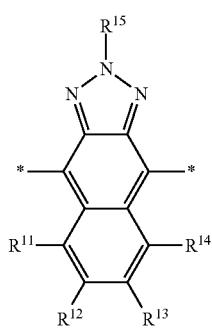
(A36) 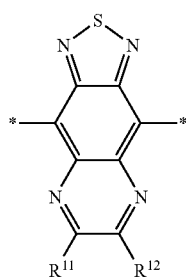
(A37) 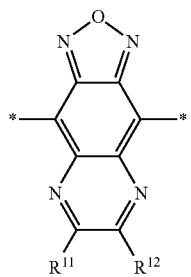
(A38) 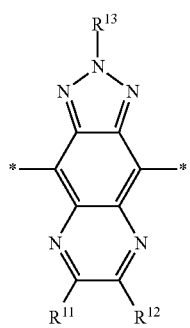
(A39) 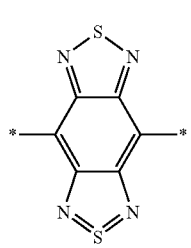
(A40) 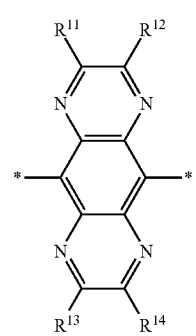
(A41) 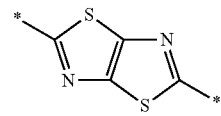
(A42) 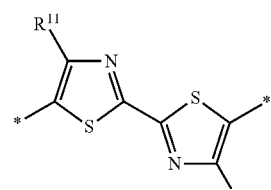
(A43) 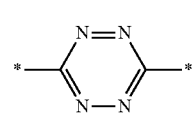
(A44) 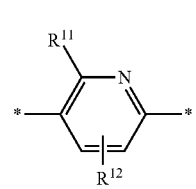
(A45) 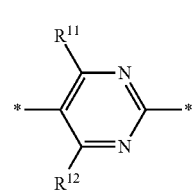
(A46) 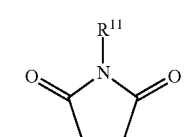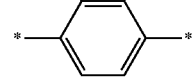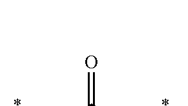
(A47) 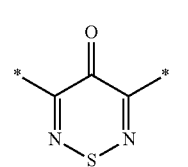

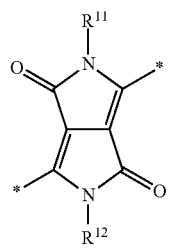 (A48)
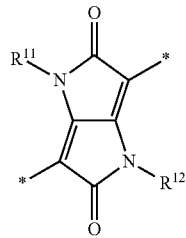 (A49)
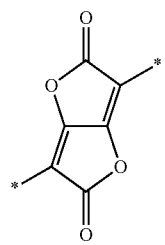 (A50)
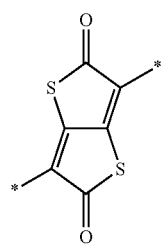 (A51)
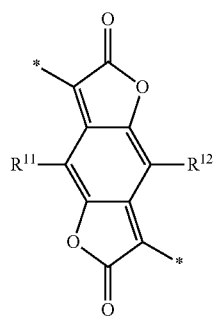 (A52)
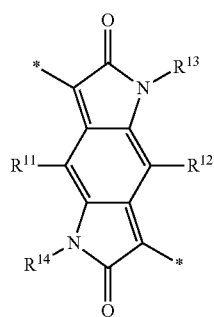 (A53)
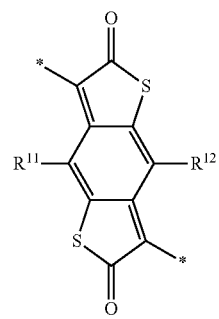 (A54)
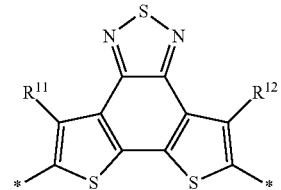 (A55)
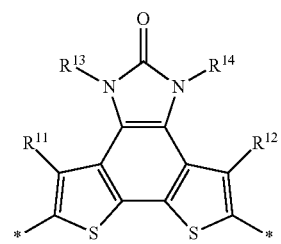 (A56)
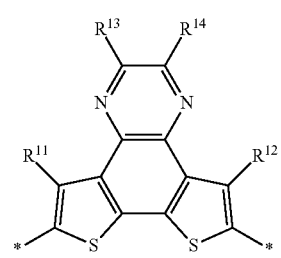 (A57)
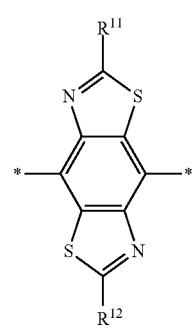 (A58)

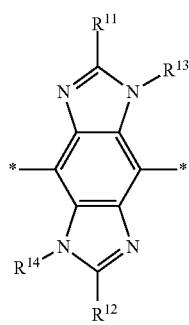
(A59)
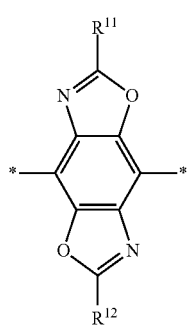
(A60)
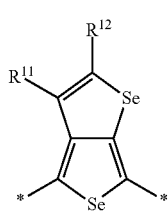
(A61)
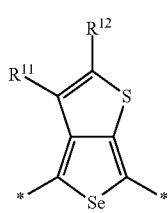
(A62)
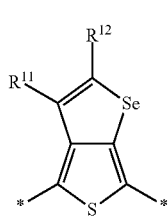
(A63)
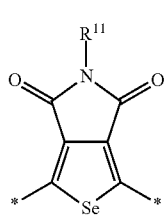
(A64)
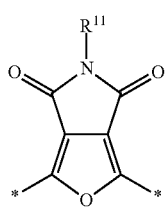
(A65)
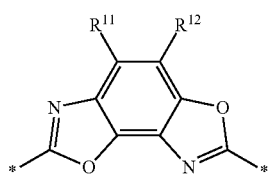
(A66)
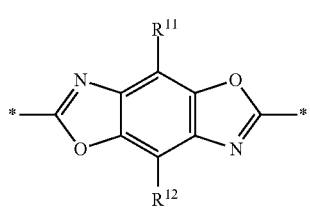
(A67)
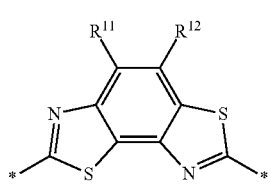
(A68)
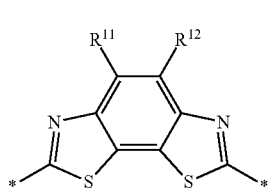
(A69)
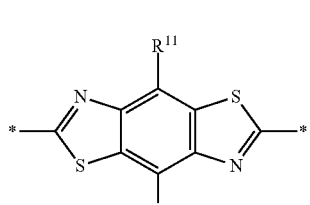
(A70)
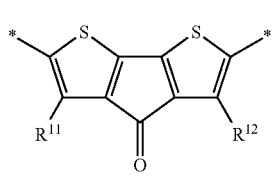
(A71)
(A72)

-continued
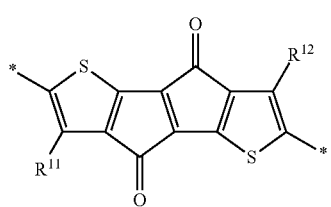
(A73)
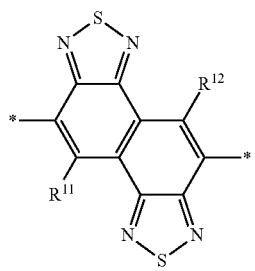
(A74)
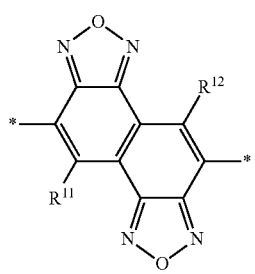
(A75)
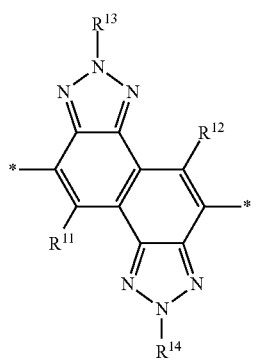
(A76)
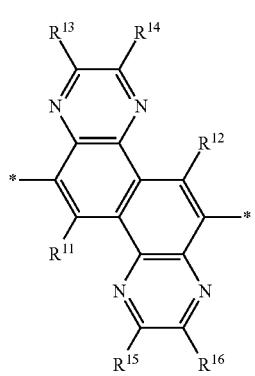
(A77)
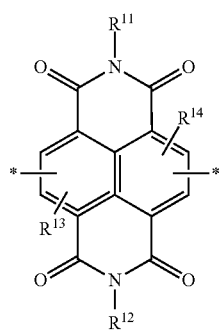
(A78)
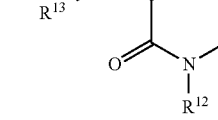
(A79)
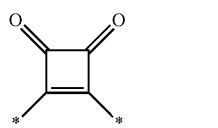
(A80)
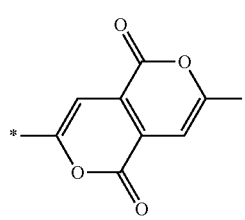
(A81)
(A82)
(A83)

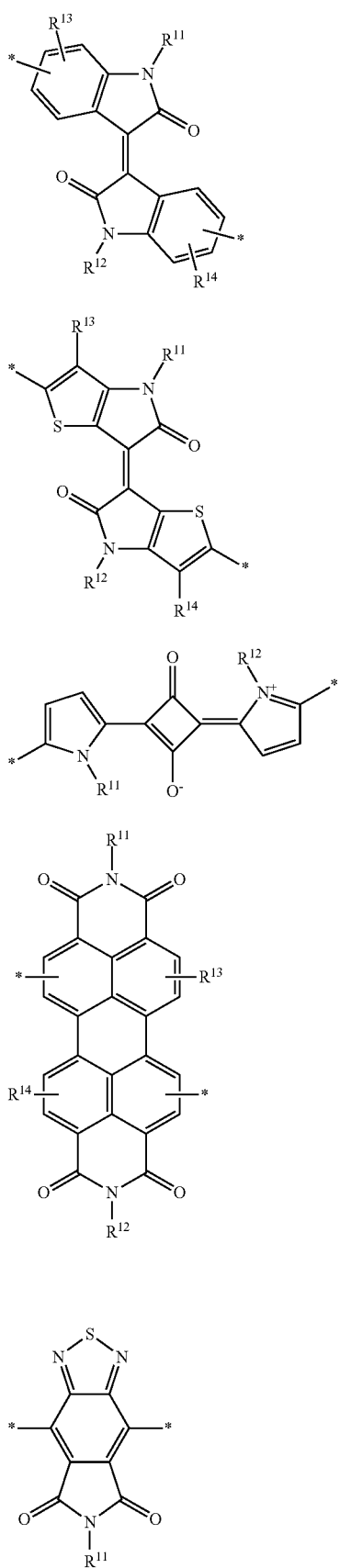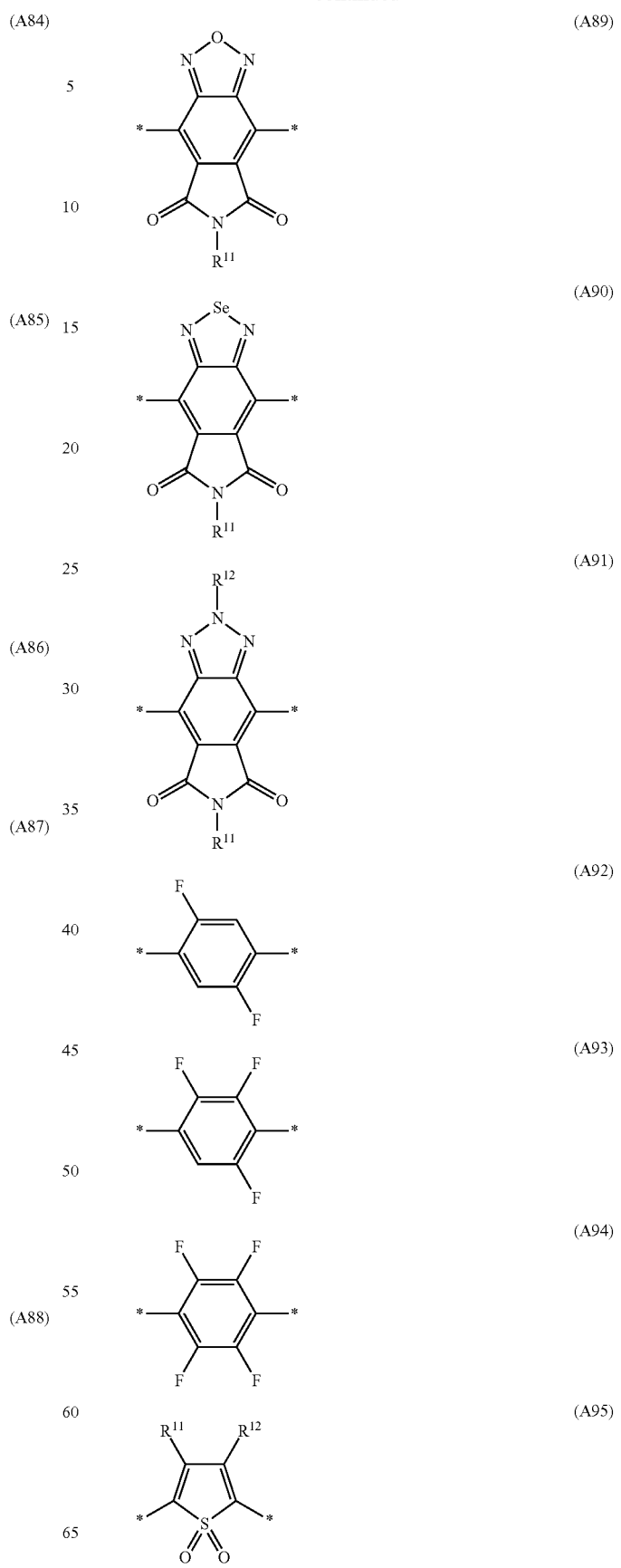

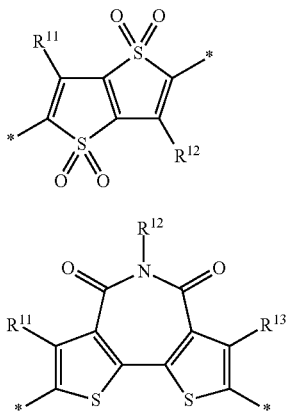
(A96)

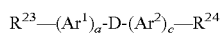
(A97)

wherein $R^{11}$, $R^{12}$, $R^{13}$, $R^{14}$, $R^{15}$ and $R^{16}$ independently of each other denote H or have one of the meanings of $R^S$ as defined above and below.

The polymer can be prepared for example from monomers selected from the following formulae $R^{23}$—$(Ar^1)_a$-D-$(Ar^2)_c$—$R^{24}$     VIa $R^{23}$-D-$(Ar^1)_a$-D-$R^{24}$     VIb $R^{23}$—$(Ar^1)_a$-A-$(Ar^2)_c$—$R^{24}$     VIc $R^{23}$—$(Ar^1)_a$—$(Ar^2)_c$—$R^{24}$     VId wherein A, D, $Ar^1$, $Ar^2$, a and b have the meanings of formula IIa and IIb, or one of the preferred meanings as described above and below, and $R^{23}$ and $R^{24}$ are, preferably independently of each other, selected from the group consisting of H, Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is halogen, preferably Cl, Br or I, Z$^{1-4}$ are selected from the group consisting of alkyl and aryl, each being optionally substituted, and two groups Z$^2$ may also together form a cyclic group.

Suitable monomers are for example selected from the following subformulae $R^{23}$—$Ar^1$-D-$Ar^2$—$R^{24}$     VIa1

$R^{23}$-D-$R^{24}$     VIa2

$R^{23}$—$Ar^1$-D-$R^{24}$     VIa3

$R^{23}$-D-$Ar^2$—$R^{24}$     VIa4

$R^{23}$-D-$Ar^1$-D-$R^{24}$     VIb1

$R^{23}$—$(Ar^1)_a$-A-$(Ar^2)_c$$R^{24}$     VIc1

$R^{23}$—$Ar^1$—$R^{24}$     VId1

$R^{23}$—$Ar^1$—$Ar^2$—$R^{24}$     VId2 wherein A, D, $Ar^1$, $Ar^2$, a, c, $R^{23}$ and $R^{24}$ are as defined in formulae VIa-VId.

The polymer can be synthesized according to or in analogy to methods that are known to the skilled person and are described in the literature. Other methods of preparation can be taken from the examples. For example, the polymers can be suitably prepared by aryl-aryl coupling reactions, such as Yamamoto coupling, Suzuki coupling, Stille coupling, Sonogashira coupling, C—H activation coupling, Heck coupling or Buchwald coupling. Suzuki coupling, Stifle coupling and Yamamoto coupling are especially preferred. The monomers which are polymerised to form the repeat units of the polymers can be prepared according to methods which are known to the person skilled in the art.

For example the polymer can be prepared by coupling one or more monomers selected from formulae VIa-VId and their subformulae in an aryl-aryl coupling reaction, wherein $R^{23}$ and $R^{24}$ are selected from Cl, Br, I, —B(OZ$^2$)$_2$ and —Sn(Z$^4$)$_3$.

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in J. Chem. Soc., Chem. Commun., 1977, 683-684. Yamamoto coupling is described in for example in T. Yamamoto et al., Prog. Polym. Sci., 1993, 17, 1153-1205, or WO 2004/022626 A1, and Stille coupling is described for example in Z. Bao et al., J. Am. Chem. Soc., 1995, 117, 12426-12435. For example, when using Yamamoto coupling, monomers having two reactive halide groups are preferably used. When using Suzuki coupling, monomers of formulae VIa-VId and their subformulae having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-ideneacetone)dipalladium(0), bis(dibenzylideneacetone)-palladium(0), or Pd(II) salts e.g. palladium acetate, with a phosphine ligand, for example triphenylphosphine, tris(ortho-tolyl)phosphine or tri(tert-butyl)phosphine. Suzuki polymerisation is performed in the presence of a base, for example sodium carbonate, potassium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

Suzuki and Stille polymerisation may be used to prepare homopolymers as well as statistical, alternating and block random copolymers. Statistical or block copolymers can be prepared for example from the above monomers of formula VI or its subformulae, wherein one of the reactive groups is halogen and the other reactive group is a boronic acid, boronic acid derivative group or and alkylstannane. The synthesis of statistical, alternating and block copolymers is described in detail for example in WO 03/048225 A2 or WO 2005/014688 A2.

The concentration of the fullerene derivatives of this invention, or of the fullerene mixture, in a formulation according to the present invention, including solvents, is preferably 0.1 to 10% by weight, more preferably 0.5 to 5% by weight. The concentration of the fullerene derivatives of this invention in a fullerene mixture, more specifically a fullerene derivative/polymer mixture according to the present invention (i.e. excluding solvents), is preferably from 10 to 90% by weight, very preferably from 33% to 80% by weight.

Another aspect of the present invention relates to a formulation comprising one or more fullerene derivatives of this invention, or a fullerene mixture as described above, and further comprising one or more solvents, preferably selected from organic solvents.

Such a formulation is preferably used as a carrier for the preparation of a semiconducting layer of an OE device, like an OPV or OPD device, wherein the fullerene derivative or fullerene mixture is for example used in the photoactive layer.

Optionally, the formulation further comprises one or more binders to adjust the rheological properties, as described for example in WO 2005/055248 A1.

The formulations according to the present invention preferably form a solution.

The invention additionally provides an electronic device comprising a fullerene derivative of this invention or fullerene mixture, or a semiconducting layer comprising it, as described above and below.

Especially preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV and OPD devices, in particular bulk heterojunction (BHJ) OPV devices and OPD devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices, preferably a fullerene mixture is used that contains a p-type (electron donor) semiconductor and an n-type (electron acceptor) semiconductor. The p-type semiconductor is for example a conjugated polymer having repeating units of formulae IIa, IIb or III, or a polymer of formula IV, V or their subformulae, as shown above, a small molecule, a mixture of a two or more polymers or mixture of one or more polymers and one or more small molecules. The n-type semiconductor is a fullerene derivative of this invention, a mixture of two or more fullerenes, at least one of which is a fullerene derivative of this invention.

The device preferably further comprises a first transparent or semi-transparent electrode on a transparent or semi-transparent substrate on one side of the active layer, and a second metallic or semi-transparent electrode on the other side of the active layer.

Preferably, the active layer according to the present invention is further blended with additional organic and inorganic compounds to enhance the device properties. For example, metal particles such as Au or Ag nanoparticules or Au or Ag nanoprism for enhancements in light harvesting due to near-field effects (i.e. plasmonic effect) as described, for example in Adv. Mater. 2013, 25 (17), 2385-2396 and Adv. Ener. Mater. 10.1002/aenm.201400206, a molecular dopant such as 2,3,5,6-tetrafluoro-7,7,8,8-tetracyanoquinodimethane for enhancement in photoconductivity as described, for example in Adv. Mater. 2013, 25(48), 7038-7044, or a stabilising agent consisting of a UV absorption agent and/or anti-radical agent and/or antioxidant agent such as 2-hydroxybenzophenone, 2-hydroxyphenylbenzotriazole, oxalic acid anilides, hydroxyphenyl triazines, merocyanines, hindered phenol, N-aryl-thiomorpholine, N-aryl-thiomorpholine-1-oxide, N-aryl-thiomorpholine-1,1-dioxide, N-aryl-thiazolidine, N-aryl-thiazolidine-1-oxide, N-aryl-thiazolidine-1,1-dioxide and 1,4-diazabicyclo[2.2.2]octane as described, for example, in WO2012095796 A1 and in WO2013021971 A1.

The device preferably may further comprise a UV to visible photo-conversion layer such as described, for example, in J. Mater. Chem. 2011, 21, 12331 or a NIR to visible or IR to NIR photo-conversion layer such as described, for example, in J. Appl. Phys. 2013, 113, 124509.

Further preferably the OPV or OPD device comprises, between the active layer and the first or second electrode, one or more additional buffer layers acting as hole transporting layer and/or electron blocking layer, which comprise a material such as metal oxides, like for example, ZTO, $MoO_x$, $NiO_x$, a doped conjugated polymer, like for example PEDOT:PSS and polypyrrole-polystyrene sulfonate (PPy:PSS), a conjugated polymer, like for example polytriarylamine (PTAA), an organic compound, like for example substituted triaryl amine derivatives such as N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), graphene based materials, like for example, graphene oxide and graphene quantum dots or alternatively as hole blocking layer and/or electron transporting layer, which comprise a material such as metal oxide, like for example, $ZnO_x$, $TiO_x$, AZO (aluminium doped zinc oxide), a salt, like for example LiF, NaF, CsF, a conjugated polymer electrolyte, like for example poly[3-(6-trimethylammoniumhexyl) thiophene], poly(9,9-bis(2-ethylhexyl)-fluorene]-b-poly[3-(6-trimethylammoniumhexyl)thiophene], or poly[(9,9-bis (3"-(N,N-dimethylamino)propyl)-2,7-fluorene)-alt-2,7-(9, 9-dioctylfluorene)], a polymer, like for example poly (ethyleneimine) or crosslinked N-containing compound derivatives or an organic compound, like for example tris (8-quinolinolato)-aluminium(III) ($Alq_3$), phenanthroline derivative or $C_{60}$ or $C_{70}$ based fullerenes, like for example, as described in Adv. Energy Mater. 2012, 2, 82-86.

In a fullerene mixture comprising a fullerene derivative and a polymer according to the present invention, the ratio polymer:fullerene derivative is preferably from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in OE devices, like BHJ OPV devices, a fullerene derivative, fullerene mixture or formulation according to the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

When preparing a suitable solution or formulation containing a mixture of a fullerene derivative (as n-typer component) and a polymer (as p-type component) according to the present invention, a suitable solvent should selected so as to ensure full dissolution of both the p-type and the n-type component, and to take into account the boundary conditions (for example rheological properties) introduced by the chosen printing method.

Organic solvents are generally used for this purpose. Typical solvents can be aromatic solvents, halogenated solvents or chlorinated solvents, including chlorinated aromatic solvents. Preferred solvents are aliphatic hydrocarbons, chlorinated hydrocarbons, aromatic hydrocarbons, ketones, ethers and mixtures thereof. Examples include, but are not limited to dichloromethane, trichloromethane, tetrachloromethane, chlorobenzene, o-dichlorobenzene, 1,2,4-trichlorobenzene, 1,2-dichloroethane, 1,1,1-trichloroethane, 1,1,2,2-tetrachloroethane, 1,8-diiodooctane, 1-chloronaphthalene, 1,8-octane-dithiol, anisole, 2-methylanisole, phenetol, 4-methyl-anisole, 3-methylanisole, 2,6-dimethylanisole, 2,5-dimethylanisole, 2,4-dimethylanisole, 3,5-dimethyl-anisole, 4-fluoroanisole, 3-fluoro-anisole, 3-trifluoro-methylanisole, 4-fluoro-3-methylanisole, 2-fluoroanisole, toluene, o-xylene, m-xylene, p-xylene, mixture of xylene o-, m-, and p-isomers, 1,2,4-trimethylbenzene, 1,2,3,4-tetra-methyl benzene, pentylbenzene, mesitylene, cumene, cymene, cyclohexylbenzene, diethylbenzene, cyclohexane, 1-methylnaphthalene, 2-methylnaphthalene, 1,2-dimethylnaphthalene, tetraline, decaline, indane, 1-methyl-4-(1-methylethenyl)-cyclohexene (d-Limonene), 6,6-dimethyl-2-methylenebicyclo[3.1.1]heptanes (β-pinene), 2,6-lutidine, 2-fluoro-m-xylene, 3-fluoro-o-xylene, 2-chloro-benzotrifluoride, 2-chloro-6-fluorotoluene, 2,3-dimethylpyrazine, 2-fluorobenzonitrile, 4-fluoroveratrol, 3-fluorobenzo-nitrile, 1-fluoro-3,5-dimethoxy-benzene, 3-fluorobenzotrifluoride, benzotrifluoride, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, 2-chlorofluorobenzene, methyl benzoate, ethyl benzoate, nitrobenzene, benzaldehyde, benzonitrile, tetrahydrofuran, 1,4-dioxane, 1,3-dioxane, morpholine, acetone, methylethylketone, ethyl acetate, n-butyl acetate, N,N-dimethylaniline, N,N-dimethylformamide, N-methylpyrrolidinone, dimethylacetamide, dimethylsulfoxide and/or mixtures thereof.

Especially preferred are solvents selected from aliphatic or aromatic hydrocarbons, or mixtures thereof, which are non-chlorinated.

Further preferred are solvents selected from non-chlorinated aliphatic or aromatic hydrocarbons, or mixtures thereof, which contain less than 5% of halogenated but non-chlorinated (e.g. fluorinated, brominated or iodinated) aliphatic or aromatic hydrocarbons, like e.g. 1,8-diiodooctane.

Preferred solvents of this type are selected from 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, N,N-dimethylformamide, 2,3-dimethylpyrazine, 2-methylanisole, phenetol, 4-methyl-anisole, 3-methylanisole, 2,5-dimethylanisole, 2,4-dimethylanisole, 3,5-dimethyl-anisole, N,N-dimethylaniline, ethyl benzoate, 1-methylnaphthalene, 2-methylnaphthalene, N-methylpyrrolidinone, dioxane, 4-isopropylbiphenyl, phenyl ether, pyridine, 1,8-octanedithiol, nitrobenzene, 1-chloronaphthalene, p-xylene, m-xylene, o-xylene or mixture of o-, m-, and p-isomers.

The OPV device can be of any OPV device type known from the literature (see e.g. Waldauf et al., *Appl. Phys. Lett.*, 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode or a conducting grid
  an optional conducting polymer layer or hole transport layer, preferably comprising an organic polymer or polymer blend, for example PEDOT:PSS (poly(3,4-ethylenedioxythiophene): poly(styrene-sulfonate), substituted triaryl amine derivatives, for example, TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF, $TiO_x$, $ZnO_x$, PFN, a poly(ethyleneimine) or crosslinked nitrogen containing compound derivatives or a phenanthroline derivatives
  a low work function electrode, preferably comprising a metal like for example aluminum, serving as cathode,
  wherein at least one of the electrodes, preferably the anode, is at least partially transparent to visible light, and
  wherein the n-type semiconductor is a fullerene derivative of this invention.

A second preferred OPV device according to the invention is an inverted OPV device and comprises the following layers (in the sequence from bottom to top):
  optionally a substrate,
  a high work function metal or metal oxide electrode, comprising for example ITO, serving as cathode, or a conducting grid
  a layer having hole blocking properties, preferably comprising a metal oxide like $TiO_x$ or $ZnO_x$, or comprising an organic compound such as polymer like poly(ethyleneimine) or crosslinked nitrogen containing compound derivatives or phenanthroline derivatives,
  a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic polymer or polymer blend, for example of PEDOT:PSS or substituted triaryl amine derivatives, for example, TBD or NBD,
  an electrode comprising a high work function metal like for example silver, serving as anode, wherein at least one of the electrodes, preferably the cathode, is at least partially transparent to visible light, and wherein the n-type semiconductor is a fullerene derivative of this invention.

In the OPV devices of the present invention the p-type and n-type semiconductor materials are preferably selected from the materials, like the polymer/fullerene systems, as described above When the photoactive layer is deposited on the substrate, it forms a BHJ that phase separates at nanoscale level. For discussion on nanoscale phase separation see Dennler et al, *Proceedings of the IEEE,* 2005, 93 (8), 1429 or Hoppe et al, *Adv. Func. Mater,* 2004, 14(10), 1005. An optional annealing step may be then necessary to optimize blend morpohology and consequently OPV device performance.

Another method to optimize device performance is to prepare formulations for the fabrication of OPV(BHJ) devices that may include additives with variable boiling points to promote phase separation in the right way. 1,8-Octanedithiol, 1,8-diiodooctane, nitrobenzene, 1-chloronaphthalene, N,N-dimethylformamide, dimethylacetamide, dimethylsulfoxide and other additives have been used to obtain high-efficiency solar cells. Examples are disclosed in J. Peet, et al, *Nat. Mater.,* 2007, 6, 497 or Fréchet et al. *J. Am. Chem. Soc.,* 2010, 132, 7595-7597.

The fullerene derivatives, fullerene mixtures and semiconducting layers of the present invention are also suitable for use as n-type semiconductor in other OE devices or device components, for example in the semiconducting channel of an OFET device, or in the buffer layer, electron transport layer (ETL) or hole blocking layer (HBL) of an OLED or OPV device.

Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a fullerene derivative of this invention, a fullerene mixture or an organic semiconducting layer according to the present invention as n-type semiconductor. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
 a source electrode,
 a drain electrode,
 a gate electrode,
 a semiconducting layer,
 one or more gate insulator layers,
 optionally a substrate.
wherein the semiconductor layer comprises a fullerene derivative of this invention or a fullerene mixture as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the fullerene derivatives, fullerene mixtures, and semiconducting layers according to the invention can be used in OLEDs, for example in the buffer layer, ETL or HBL of an OLED. The OLED device can be used for example as the active display layer in a flat panel display device, or as the backlight of a flat panel display like for example a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer.

The fullerene derivatives, fullerene mixture or semiconducting layer according to the present invention may be employed in one or more of the ETL, HBL or buffer layer, especially their water-soluble derivatives (for example with polar or ionic side groups) or ionically doped forms. The processing of such layers, comprising a semiconductor material of the present invention, for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128, O'Malley et al, *Adv. Energy Mater.* 2012, 2, 82-86 and the literature cited therein.

According to another use, the fullerene derivatives, fullerene mixtures, and materials according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of a fullerene derivative according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, ($NO_2^+$) ($SbF_6^-$), ($NO_2^+$) ($SbCl_6^-$), ($NO_2^+$) ($BF_4^-$), $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of a fullerene derivative of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

According to another use, the fullerene derivatives and fullerene mixtures according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The fullerene derivatives, fullerene mixtures, and materials according to the present invention may also be combined with photoisomerisable compounds and/or chromophores for use in or as photoalignment layers, as described in US 2003/0021913 A1.

According to another use the fullerene derivatives, fullerene mixtures, and materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius. The values of the dielectric constant ∈ ("permittivity") refer to values taken at 20° C. and 1,000 Hz.

The invention will now be described in more detail by reference to the following examples, which are illustrative only and do not limit the scope of the invention.

A) Compound Examples

Comparison Example 1

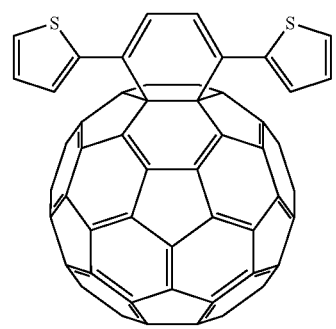

Fullerene C1 and its preparation are disclosed in *Macromol. Rapid Commun.* 2007, 28, 1345-1349.

Comparison Example 2

Example C2.1

2,5-Bis(trimethylsilyl)thiophene

Under a argon atmosphere, a solution of thiophene (3) (50 mmol, 4.21 g) in 80 cm³ dry THF is cooled to −78° C., then n-butyllithium (105 mmol, 66 cm³, 1.6 M in hexane) is added dropwise. The solution is stirred at −78° C. for 60 minutes and then is warmed to room temperature for 30 minutes. After the solution is cooled to −78° C. again, trimethylsilyl chloride (SiMe₃Cl) (110 mmol, 14.0 cm³) is added dropwise and the reaction mixture is stirred for 60 minutes at −78° C. then allowed to warm to room temperature over another 12 hours. The reaction is quenched with water (100 cm³) and an organic layer separated. The aqueous layer is extracted with hexanes (3×50 cm³) and the combined organic extracts are dried with anhydrous Na₂SO₄ and concentrated by rotary evaporation to give colorless oil. This oil is directly used for next step without further purification. (8.7 g, 75%).

Example C2.2

2,5-Bis(trimethylsilyl)thiophene-1,1-dioxide

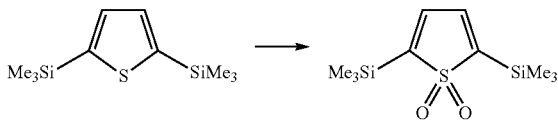 [SMILES: C[Si](C)(C)c1ccc([Si](C)(C)C)s1 ; C[Si](C)(C)C1=CC=C([Si](C)(C)C)S1(=O)=O]

2,5-bis(trimethylsilyl)thiophene (30 mmol, 6.96 g) is dissolved in 600 cm³ of dry methylene chloride, and m-MCPA (90 mmol, 20.17 g, 77% purity) is added stepwise. The mixture is stirred at 21° C. for 24 hours and filtered and washed first with 10% NaHCO₃ and then with distilled water. The aqueous layer is extracted with methylene chloride (3×50 cm³) and the combined organic extracts are dried with anhydrous Na₂SO₄ and concentrated by rotary evaporation to give colorless oil. The oil obtained in this way is chromatographed on silica gel using hexanes/methylene chloride 50:50. A total of 5.1 g (65% yield) of 2,5-bis(trimethylsilyl)thiophene-1,1-dioxide as a white crystalline material is obtained. Mass (m/z, DART): 261.08 ([M+H]⁺).

Example C2.3

2,5-Diiodothiophene-1,1-dioxide

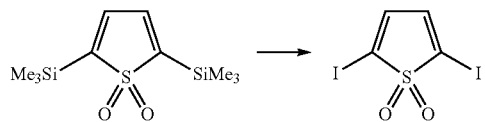 [SMILES: C[Si](C)(C)C1=CC=C([Si](C)(C)C)S1(=O)=O ; O=S1(=O)C(I)=CC=C1I]

2,5-Bis(trimethylsilyl)thiophene-1,1-dioxide (9.6 mmol, 2.5 g) is reacted with iodine (I₂) (38.4 mmol, 9.75 g) in the presence of AgBF₄ (57.6 mmol, 11.2 g) in methylene chloride (200 cm³) at 0° C. for 1 h. The reaction is quenched with ice water, then washed three times with sodium bisulfite (NaHSO₃) to remove un-reacted iodine, followed by the NaHCO₃ solution, brine, and the combined organic extracts are dried with anhydrous Na₂SO₄. After concentrated by rotary evaporation, the crude material is recrystallized from hexane to give white solid (2.9 g, 82%).

Example C2.4

2Ethyl-5-tri-n-butylstannyl thiophene

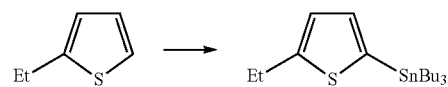

Under a argon atmosphere, a solution of 2-ethyl-thiophene (40 mmol, 4.63 g) in 50 cm³ dry tetrahydrofuran is cooled to −78° C., then n-butyllithium (n-BuLi) (48 mmol, 30 cm³, 1.6 M in hexanes) is added dropwise. The solution is stirred at −78° C. for 60 minutes and then is warmed to room temperature for 30 minutes. After the solution is cooled to −78° C. again, tributylstannyl chloride (SnBu₃Cl) (52.8 mmol, 17.2 g) is added dropwise and the reaction mixture is stirred for 60 minutes at −78° C. then allowed to warm to room temperature over another 12 hours. The reaction is quenched with water (100 cm³) and the organic layer separated. The aqueous layer is extracted with methylene chloride (3×50 cm³) and the combined organic extracts are dried with anhydrous Na₂SO₄ and concentrated by rotary evaporation to give yellow oil. This oil is directly used for the next step without further purification. ¹H NMR (300 MHz, CDCl₃) δ: 6.99 (d, 1H), 6.92 (d, 1H), 2.91 (m, 2H), 1.34-0.86 (m, 30H).

Example C2.5

5,5″-Bisethyl-2,2′:5′,2″-terthiophene-1′,1′-Dioxide

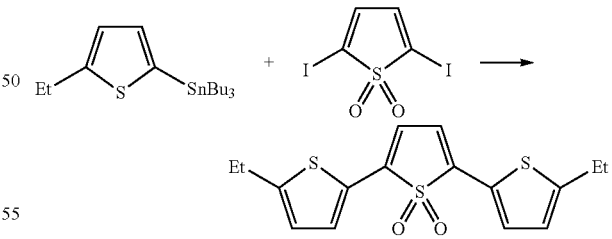

Tris(dibenzylideneacetone)dipalladium(0) (0.750 mmol, 687 mg) and triphenylarsine (AsPh₃)(3.00 mmol, 919 mg) are dissolved in 30 cm³ of anhydrous toluene, and the solution is stirred for 30 min. Then a toluene solution containing 1.84 g (5.00 mmol) of 2,5-diiodothiophene-1,1-dioxide and 15 mmol (6.0 g) of 2-ethyl-5-tri-n-butylstannyl thiophene is added, and the mixture is refluxed for other 12 hours. After the solvent is evaporated, the crude product is purified by column chromatography on silica gel using methylene chloride to afford a red polycrystalline product (0.6 g, 36% yield). $^1$H NMR (300 MHz, CDCl$_3$) δ: 7.45 (d, 2H), 6.81 (d, 2H), 6.62 (s, 2H), 2.88 (m, 4H), 1.34 (t, 6H).

Example C2.6

Fullerene C2

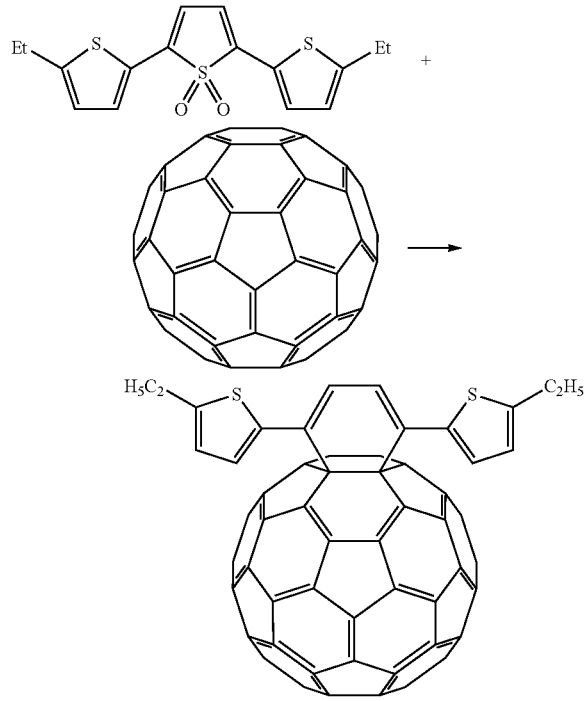

A mixture of C$_{60}$ (576.0 mg, 0.80 mmol) and 5,5"-bisethyl-2,2':5',2"-terthiophene-1',1'-dioxide (280.0 mg, 0.80 mmol) in toluene (400 cm$^3$) is heated to reflux for 48 hours. The reaction is cooled down and the solvent is removed under reduced pressure. The crude reaction mixture is purified by column chromatography on an silica gel column using decalin as eluent, followed by final purification with intermediate pressure liquid chromatography using a Buckyprep column (Nacalai) (eluent: toluene) to afford (150 mg, 19%) as a brown solid. Mass (m/z, MALDI-TOF): 994.07 ([M+H]$^+$).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Patent Application No. 61/876,427, filed Sep. 11, 2013 are incorporated by reference herein.

Example 1

Example 1.1

2-hexyl-5-tri-n-butylstannyl thiophene

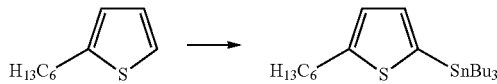

Under a argon atmosphere, a solution of 2-hexyl-thiophene (100 mmol, 16.8 g) in 100 cm$^3$ of dry tetrahydrofuran is cooled to −78° C., then n-butyllithium (n-BuLi) (110 mmol, 44 cm$^3$, 2.5 M in hexanes) is added dropwise. The solution is stirred at −78° C. for 60 minutes and then is warmed to room temperature for 30 minutes. After the solution is cooled to −78° C. again, tributylstannyl chloride (SnBu$_3$Cl) (115.5 mmol, 37.6 g) is added dropwise and the reaction mixture is stirred for 60 minutes at −78° C. then allowed to warm to room temperature over another 12 hours. The reaction is quenched with water (200 cm$^3$) and the organic layer separated. The aqueous layer is extracted with methylene chloride (3×100 cm$^3$) and the combined organic extracts are dried with anhydrous Na$_2$SO$_4$ and concentrated by rotary evaporation to give yellow oil. This oil is directly used for the next step without further purification. $^1$H NMR (300 MHz, CDCl$_3$) δ: 6.98 (d, 1H), 6.90 (d, 1H), 2.87 (m, 2H), 1.55-0.91 (m, 20H), 0.89 (m, 18H).

Example 1.2

5,5"-Bishexy-2,2':5',2"-terthiophene-1',1'-Dioxide

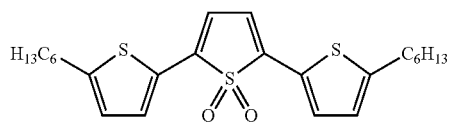

Tris(dibenzylideneacetone)dipalladium(0) (0.750 mmol, 687 mg) and triphenylarsine (AsPh$_3$)(3.00 mmol, 919 mg) are dissolved in 30 cm$^3$ of anhydrous toluene, and the solution is stirred for 30 minutes. Then a toluene solution containing 1.84 g (5.00 mmol) of 2,5-Diiodothiophene-1,1-dioxide and 15 mmol (6.9 g) of 2-hexyl-5-tri-n-butylstannyl thiophene is added, and the mixture is refluxed for other 12 hours. After the solvent is evaporated, the crude product is chromatographed on silica gel using methylene chloride to afford a red color solid (0.7 g, 31% yield). Mass (m/z, DART): 448.17 ([M]$^+$)

Example 1.3

Fullerene 1

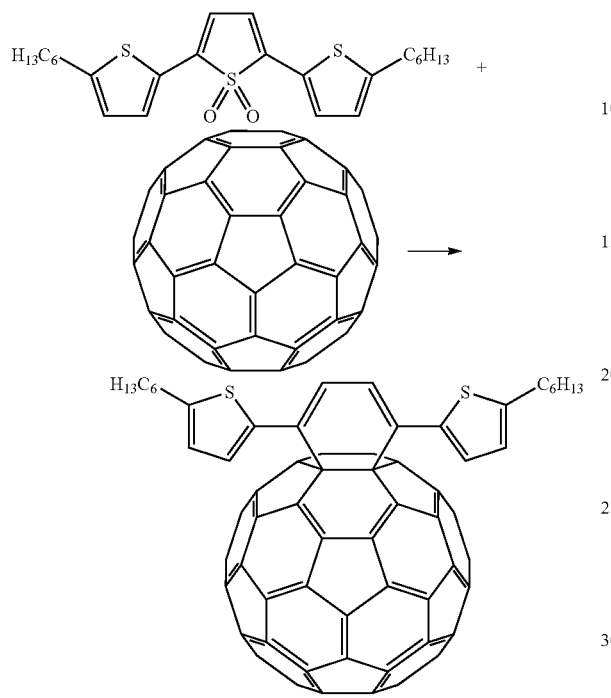

A mixture of $C_{60}$ (360.0 mg, 0.50 mmol) and 5,5"-bishexyl-2,2':5',2"-terthiophene-1',1'-dioxide (220 mg, 0.50 mmol) in toluene (250 cm³) is heated to reflux for 48 hours. The reaction is cooled down and the solvent is removed under reduced pressure. The crude reaction mixture is purified by column chromatography on an silica gel column using decalin as the eluent, followed by final purification with intermediate pressure liquid chromatography using a Buckyprep column (Nacalai) (eluent: toluene) to afford (130 mg, 24%) as a brown solid. ¹H NMR (300 MHz, CDCl₃) δ: 7.25 (d, 2H), 6.76 (d, 2H), 6.32 (s, 2H), 2.87 (t, 4H), 1.74 (m, 4H), 1.40-1.25 (m, 12H), 0.90 (t, 6H). Mass (m/z, MALDI-TOF): 1106.11 ([M+H]⁺).

Example 2

Example 2.1

2,5-bis(4-hexylphenyl)thiophene

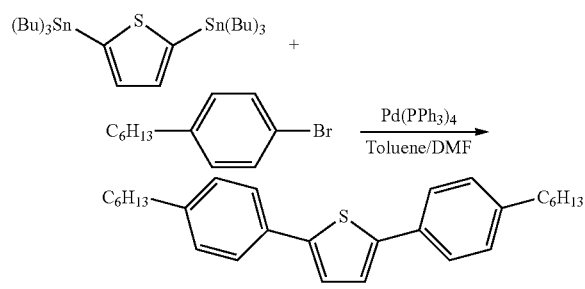

An oil bath is raised to 120° C. To a clean dry 250 cm³ flask with stir bar is added 1.85 g (7.67 mmol, 2.4 eq) of 1-bromo-4-n-hexylbenzene, 2.11 g (3.20 mmol, 1 eq) of 2,5-bis(tributylstannyl)thiophene and 739 mg (0.639 mmol, 0.2 eq) of tetrakis(triphenylphosphine)palladium(0). The first two reagents are added by weight using a dropper. The flask is sealed and pump purged three times with nitrogen and vacuum. Anhydrous toluene (25.6 cm³) and anhydrous DMF (6.4 cm³) are added by syringe. The reaction is lowered into an oil bath at 120° C. and allowed to stir overnight. After one night the reaction is yellow with black precipitate. The reaction mixture is cooled, pulled through a silica plug with generous DCM and the solvent is removed using reduced pressure in the presence of silica gel. The crude material is purified by column chromatography using silica and hexane followed by hexane and 1% ethyl acetate. Material is carried directly on to the next reaction.

Example 2.2

2,5-bis(4-hexylphenyl)-1λ⁶-thiophene-1,1-dione

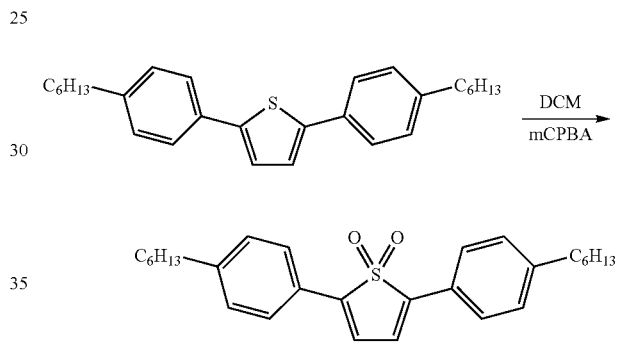

To a clean dry 250 cm³ round bottom flask with a stir bar is added 1.34 g (3.93 mmol, 1 eq) 2,5-bis(4-hexylphenyl)thiophene and 3.96 g (17.68 mmol, 77% or less by weight, 4.5 eq) mCPBA. The flask is sealed and purged three times with nitrogen and vacuum. Anhydrous DCM (78.6 cm³) is added by syringe and the reaction is allowed to stir at 23° C. for 18 hours. The reaction mixture is rotary evaporated onto silica and purified by column chromatography using silica and 5-7% ethyl acetate in hexane as eluent. The title product is obtained (196.4 mg, 14.1% yield over two steps) as a light yellow waxy solid. ¹H NMR (500 MHz, CD₂Cl₂ (set to 5.3 ppm)) δ 7.665 (d (q), J=8.5 Hz, 4H), 7.287 (d (q), J=8.5 Hz, 4H), 6.995 (s, 2H), 2.640 (t, J=7.5 Hz, 4H), 1.9-0.8 (m, 22H).

Example 2.3

Fullerene 2

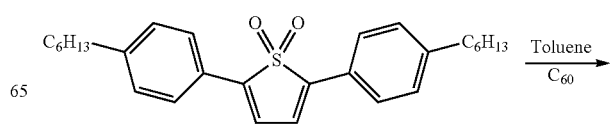

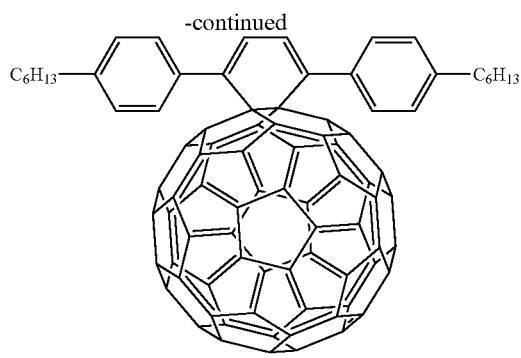

An oil bath is brought to 125° C. To a clean dry 1 dm$^3$ round bottom with a stir bar is added 964.5 mg of C$_{60}$ fullerene (1.34 mmol, 3 eq) and 620 cm3 of toluene. The round bottom is fitted with a condenser and allowed to stir and heat to reflux before 194.8 mg of 2,5-bis(4-hexylphenyl)-1λ$^6$-thiophene-1,1-dione (0.446 mmol, 1 eq) is added by syringe in 50 cm$^3$ of toluene. The reaction is allowed to reflux and stir for 2 days at which point it is cooled and the solvent is removed under reduced pressure. The crude material is purified by HPLC using a column with cosmosil buckyprep material as the stationary phase (from Nacalai Tesque; pyrenylpropyl group bonded silica) and toluene as the mobile phase. Fractions containing pure product are combined and solvent removed using rotary evaporation. The sample is left in an oven overnight at 70° C. under reduced pressure to remove residual solvent. The product is isolated (183 mg, 37.5%) as a brown crystalline solid. $^1$H NMR (500 MHz, CDCl$_3$ (set to 7.26 ppm)) δ 7.743 (br, 4H), 7.315 (d, J=8.5 Hz, 4H), 6.187 (s, 2H), 2.662 (t, J=8.0 Hz, 4H), 1.8-0.8 (m, 22H).

Example 3

Example 3.1

1-bromo-4-(hexyloxy)benzene

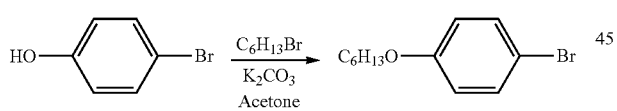

An oil bath is raised to 65° C. To a 500 cm$^3$ round bottom with stir bar is added 10 g (57.8 mmol, 1.0 eq) of 4-bromophenol and 26.36 g (190.7 mmol, 3.3 eq) of potassium carbonate, followed by 202.3 cm$^3$ of acetone. The vessel is sealed, fitted with a condenser and purged with a constant flow of argon for ten minutes. After the ten minutes have elapsed, 8.9 cm$^3$ (64 mmol, 1.1 eq) of n-hexylbromide is added slowly by syringe and the reaction is stirred at reflux for one day in the prepared heated oil bath. After confirming the desired reaction by thin layer chromatography (silica, hexanes), the crude reaction mixture is filtered to remove potassium carbonate. Water is added to the filtrate, which is extracted with diethyl ether twice. The ether extractions are then dried with magnesium sulfate which is subsequently removed by filtration. The solvent is removed at reduced pressure and the crude material is purified by chromatography using silica and hexanes to give 13.96 g (93.9% yield) of the title product as a clear liquid showing the correct molecular ion by GCMS. $^1$H NMR (500 MHz, CDCl$_3$ (set to 7.26 ppm)) δ 7.355 (m, 2H), 6.770 (m, 2H), 3.912 (t, J=6.75 Hz, 2H), 1.764 (m, 2H), 1.49-1.40 (m, 2H), 1.37-1.30 (m, 4H), 0.905 (t, J=7.0, 3H).

Example 3.2

[4-(hexyloxy)phenyl]boronic acid

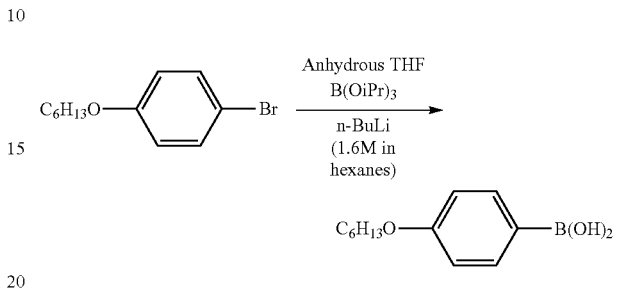

To a clean dry 500 cm$^3$ round bottom flask with stir bar is added 10 g (38.88 mmol, 1.0 eq) of the 1-bromo-4-(hexyloxy)benzene. The flask is then capped and purged three times with nitrogen and vacuum. Anhydrous tetrahydrofuran (171.2 cm3) is added by syringe, and the mixture is cooled over 30 minutes with stirring to −78° C. using an acetone, dry ice bath. To this mixture is added 29.16 cm$^3$ (46.66 mmol, 1.2 eq) of 1.6 molar n-butyllithium solution in hexanes, over 45 minutes dropwise using a syringe and syringe pump. The mixture is then stirred for an additional 45 minutes at −78° C., after which time 10.78 cm$^3$ (46.66 mmol, 1.2 eq) of triisopropylborate is added. The reaction is then allowed to warm to room temperature for one hour. Water (250 cm$^3$) is added to the reaction mixture and a white solid precipitate formed. The white solid is filtered, and washed with hexanes. Rotary evaporation is used to remove the hexane and a significant amount of the water from the filtrate. The additional precipitate is also collected by filtration. The two filtered portions are pooled together to give 7.13 g (82.6% yield). The crude product is used in the next reaction without further purification.

Example 3.3

2,5-bis[4-(hexyloxy)phenyl]thiophene

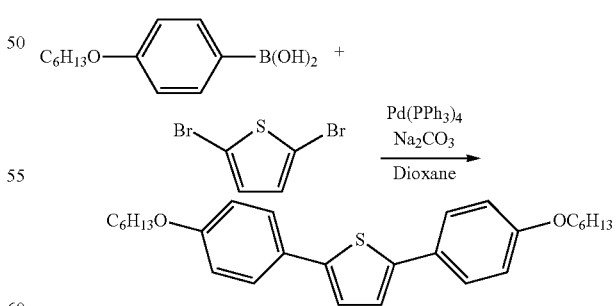

An oil bath is raised to 90° C. and a 2 molar solution of sodium carbonate is prepared. To a clean dry 250 cm$^3$ round bottom flask with stir bar is added 3.44 g (15.5 mmol, 2.5 eq) of the [4-(hexyloxy)phenyl]boronic acid and 358 mg (0.310 mmol, 0.05 eq) of tetrakis(triphenylphosphine) palladium (0). The flask is sealed and pump-purged three times with nitrogen and vacuum. Anhydrous dioxane (62 cm³) is added by syringe, followed by 0.70 cm³ (6.20 mmol, 1 eq,) of 2,5-dibromothiophene, and 74.4 cm³ of the 2 M sodium carbonate solution. The reaction is lowered into an oil bath at 90° C. and allowed to stir for two days. Thin layer chromatography (silica and 4:1 hexanes:DCM) and direct exposure mass spectrometry confirmed a successful reaction. The reaction mixture is cooled, and 10% HCl (by volume, approximately 1.22 M) is added slowly. The reaction mixture is then transferred to a separatory funnel where ethyl acetate and more 10% HCl (by volume, approximately 1.22 M) solution are added. After agitation the aqueous phase is separated and it is noted that significant solid had precipitated in the organic phase. This shimmering white solid (2.488 g) is removed by filtration. The filtrate is returned to the separatory funnel and washed twice with water, aided by some brine. The organic layer is dried with magnesium sulfate and filtered through a small silica plug to give an amber solution. The solvent is removed by rotary evaporation. Additional white solid is observed to precipitate and is removed by filtration (0.121 g). In total, 2.609 g (96.3% yield) of white material is collected. This solid is used in the next reaction without further purification. $^1$H NMR (500 MHz, CDCl$_3$ (set to 7.26 ppm)) δ 7.524 (d, J=9.0 Hz, 4H), 7.135 (s, 2H), 6.906 (d, J=8.5 Hz, 4H), 3.982 (t, J=6.75 Hz, 4H), 1.794 (m, 4H), 1.51-1.43 (m, 4H), 1.39-1.31 (m, 8H), 0.913 (t, J=7.0, 6H).

Example 3.4

2,5-bis[4-(hexyloxy)phenyl]-1λ$^6$-thiophene-1,1-dione

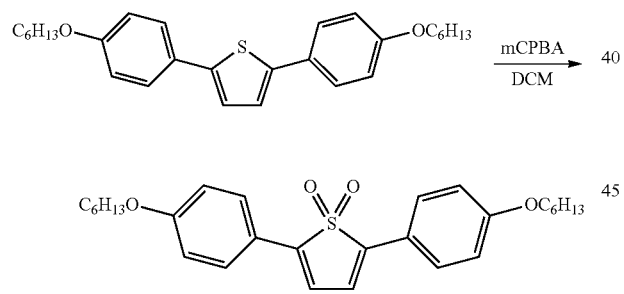

To a clean dry 250 cm round bottom flask with a stir bar is added 2.75 g (6.30 mmol, 1 eq) of 2,5-bis[4-(hexyloxy) phenyl]thiophene and 6.352 g (28.34 mmol, 77% or less by weight, 4.5 eq) of mCPBA. The reactants are washed into the flask with dichloromethane (126 cm³) and the reaction is allowed to stir at 23° C. for 18 hours. A room temperature water bath is added to cool the reaction. After 18 hours, dichloromethane is added until everything went into solution. The entire reaction mixture is then rotary evaporated onto silica and purified by column chromatography using silica and 1:1 Hexanes:DCM as eluent The title product is obtained (440 mg, 15.1% yield over two steps) as a light yellow waxy solid. $^1$H NMR (500 MHz, CDCl$_3$ (set to 7.26 ppm)) δ 7.708 (d (q), J=8.5 Hz, 4H), 6.963 (d (q), J=9.0 Hz, 4H), 6.845 (s, 2H), 4.002 (t, J=6.75 Hz, 4H), 1.798 (m, 4H), 1.51-1.42 (m, 4H), 1.38-1.31 (m, 8H), 0.914 (t, J=7.0, 6H).

Example 3.5

Fullerene 3

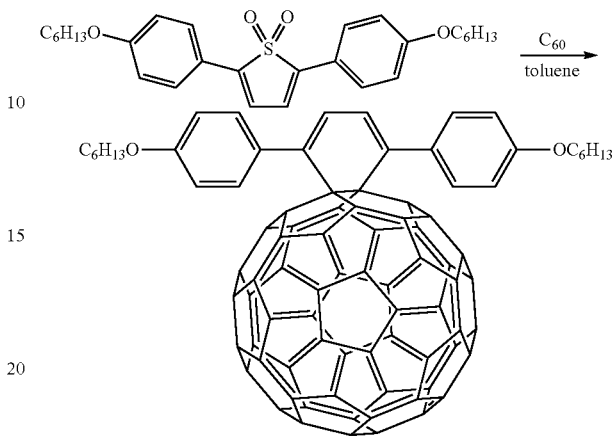

An oil bath is brought to 125° C. To a clean dry 2 dm³ round bottom with a stir bar is added 2.03 g of C$_{60}$ fullerene (2.82 mmol, 3 eq) and 1.308 dm³ of toluene. The round bottom is fitted with a condenser and allowed to stir and heat to reflux before 440 mg of 2,5-bis[4-(hexyloxy)phenyl]-1λ$^6$-thiophene-1,1-dione (0.939 mmol, 1 eq) is added by syringe in 100 cm³ of toluene. The reaction is allowed to reflux and stir for 2 days at which point it is cooled and the solvent is removed under reduced pressure. The crude material is purified by flash chromatography using a normal silica and 1:1 ODCB:Hexane as eluent. The sample is left in an oven overnight at 70° C. under reduced pressure to remove residual solvent. The product is isolated (677 mg, 64.1%) as a brown crystalline solid. $^1$H NMR (500 MHz, toluene-d$_8$ (methyl set to 2.09 ppm)) δ 7.740 (br, 4H), 7.939 (d, J=9.0 Hz, 4H), 6.056 (s, 2H), 3.653 (t, J=6.75 Hz, 4H), 1.629 (m, 4H), 1.38-1.17 (m, 12H), 0.893 (t, J=7.0, 6H).

Example 4

Example 4.1

2-(2-ethylhexyl)thiophene

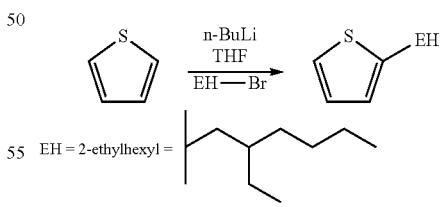

To a clean dry 1 dm³, 3-necked round bottom flask with stir bar and condenser is added 80.06 cm³ (1000 mmol, 8 eq) of thiophene. The flask is then capped and purged three times with nitrogen and vacuum. Anhydrous tetrahydrofuran (223.8 cm³) is added by syringe, and the mixture is cooled over 30 minutes with stirring to 0° C. using an ice bath. To this mixture is added 102 cm³ (162.5 mmol, 1.3 eq) of 1.6 molar n-butyllithium solution in hexanes, over 1 hour dropwise using a syringe and syringe pump at 0° C. The mixture is then stirred for an additional 30 minutes at 0° C., after which time 22.2 cm³ (125 mmol, 1 eq) of 1-bromo-2 ethylhexane is added cautiously at 0° C. The reaction is allowed to warm to room temperature briefly and then stirred at 60° C. overnight. After cooling, water is added to quench the reaction mixture. The crude mixture is extracted twice with hexanes. The organic layer is dried with magnesium sulfate and filtered. The solvent is removed by rotary evaporation to give 24.34 cm3 of crude product as an oil. Chromatography on silica in hexanes gave 18.96 g (77.3% yield) of pure product as an oil after rigorous removal of solvent. ¹H NMR (500 MHz, CDCl₃ (set to 7.26 ppm)) δ 7.109 (d, J=5.5 Hz, 1H), 6.914 (dd, J=5.0 Hz, J=3.5 Hz, 1H), 6.756 (d, J=3.5 Hz, 1H), 2.762 (d, J=6.5 Hz, 2H), 1.575 (m, 1H), 1.38-1.23 (m, 8H), 0.886 (t, J=7.5, 3H), 0.886 (t, J=7.5, 3H).

Example 4.2

Tributyl[5-(2-ethylhexyl)thiophen-2-yl]stannane

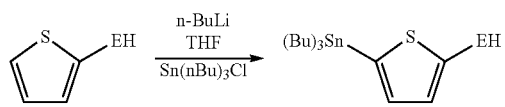

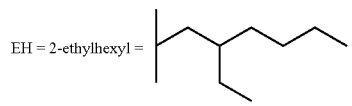

To a clean dry 100 cm³ round bottom flask with stir bar is added 2.40 g (12.22 mmol, 1 eq) of the 2-(2-ethylhexyl) thiophene by weight using a dropper. The flask is then capped and purged three times with nitrogen and vacuum. Anhydrous tetrahydrofuran (15 cm³) is added by syringe, and the mixture is cooled over 30 minutes with stirring to −78° C. using an acetone dry ice bath. To this mixture is added 9.17 cm³ (14.67 mmol, 1.2 eq) of 1.6 molar n-butyl-lithium solution in hexanes, over 30 minutes dropwise using a syringe and syringe pump at −78° C. The mixture is then stirred for an additional 30 minutes at −78° C., after which time it is warmed to room temperature using a water bath for 30 minutes and then cooled back to −78° C. After equilibrating for 30 minutes, 4.31 cm³ (15.89 mmol, 1.3 eq) of tributylstannyl chloride is added dropwise using a syringe and syringe pump over 30 minutes. Upon completion of the addition the reaction is stirred at −78° C. for one hour and allowed to warm to room temperature and stir overnight. A white precipitate appeared overnight. Water is added and the reaction mixture is transferred to a separatory funnel. The organic layer is removed and the remaining water layer is extracted with dichloromethane three times. The combined organic phases are dried with magnesium sulfate and filtered. The solvent is removed by rotary evaporation to give the crude product as an oil which is used directly in the next reaction without further manipulation. ¹H NMR (500 MHz, CDCl₃ (set to 7.26 ppm)) δ 6.979 (td, J=11.5 Hz, J=3.0 Hz, 1H), 6.878 (d, J=3.0 Hz, 1H), 2.800 (t, J=7.0 Hz, 2H), 1.70-0.75 (m, 42H).

Example 4.3

2,5-bis[5-(2-ethylhexyl)thiophen-2-yl]-1λ⁶-thiophene-1,1-dione

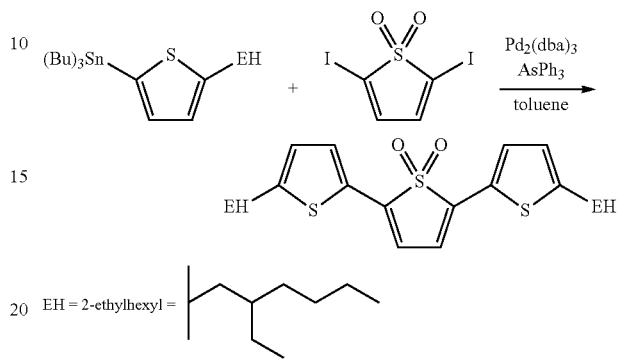

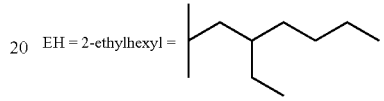

An oil bath is brought to 125° C. To the crude tributyl [5-(2-ethylhexyl)thiophen-2-yl]stannane, (assumed 5.934 g, 12.23 mmol, 3 eq) in a 250 cm³ 3-neck round bottom flask with a stir bar is added 1.5 g (4.08 mmol, 1 eq,) of 2,5-diiodothiophene-1,1-dioxide. The flask is fitted with a condenser, capped with a rubber stoppers and purged three times with nitrogen and vacuum. Anhydrous toluene (~60 cm³) is then added by syringe. To a second clean dry 100 cm³ flask with stir bar is added 560.0 mg (0.612 mmol, 0.15 eq, 915.72 g/mol) of tris(dibenzylideneacetone)dipalladium (0) and 749.1 mg (2.45 mmol, 0.6 eq) of triphenylarsine. This flask is capped with a rubber stopper and also purged three times with nitrogen and vacuum. Anhydrous toluene (~25 cm³) is added to the catalyst mixture which is then allowed to stir at room temperature. After 30 minutes the catalyst mixture is transferred by syringe from the 100 cm³ flask to the 250 cm³ flask. An additional 35 cm³ of anhydrous toluene is used to wash everything from one flask to another using the same syringe. The 250 cm³ flask is dropped into the 125° C. bath and allowed to stir overnight. The reaction mixture is then cooled, rotary evaporated onto silica and purified twice by column chromatography on silica using 2-5% ethyl acetate in hexane followed by 1% ethyl acetate in hexane to give 236 mg (11.5% yield) of the desired product as a red solid. ¹H NMR (500 MHz, CDCl₃ (set to 7.26 ppm)) δ 7.452 (d, J=4.0 Hz, 2H), 6.784 (d, J=3.5 Hz, 2H), 6.621 (s, 2H), 2.769 (d, J=6.5 Hz, 4H), 1.39-1.21 (m, 18H), 0.93-0.84 (m, 12H).

Example 4.4

Fullerene 4

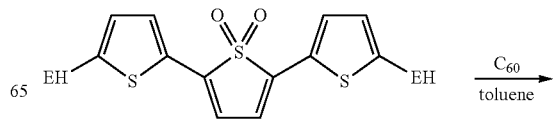

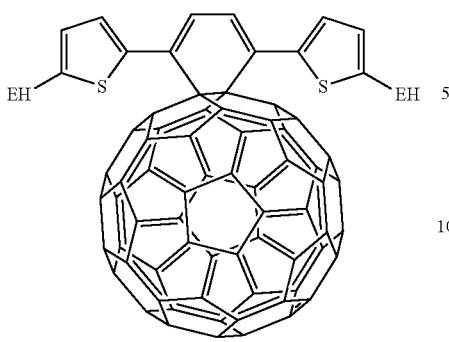

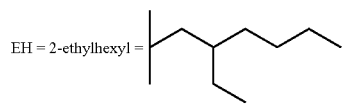

EH = 2-ethylhexyl =

An oil bath is brought to 125° C. To a clean dry 2 dm³ round bottom with a stir bar is added 2.00 g of $C_{60}$ fullerene (2.78 mmol, 5.94 eq) and 1.4 dm³ of toluene. The round bottom is fitted with a condenser and allowed to stir and heat to reflux before 236 mg of 2,5-bis[5-(2-ethylhexyl)thiophen-2-yl]-1$\lambda^6$-thiophene-1,1-dione (0.468 mmol, 1 eq) is added by syringe in 100 cm³ of toluene. The reaction is allowed to reflux and stir for 2 days at which point it is cooled and the solvent is removed under reduced pressure. The crude material is purified by HPLC using a column with cosmosil buckyprep material as the stationary phase (from Nacalai Tesque; pyrenylpropyl group bonded silica) and toluene as the mobile phase. Fractions containing pure product are combined and solvent removed using rotary evaporation. The sample is left in an oven overnight at 70° C. under reduced pressure to remove residual solvent. The product is isolated (90 mg, 16.6%) as a brown crystalline solid. ¹H NMR (500 MHz, toluene-d₈ (methyl set to 2.09 ppm)) δ 7.198 (dd, J=3.5 Hz, J=2.0 Hz 2H), 6.591 (d, J=3.5 Hz, 2H), 6.185 (s, 2H), 2.659 (d, J=7.0 Hz, J=3.0 Hz, 4H), 1.559 (m, 2H), 1.37-1.17 (m, 16H), 0.93-0.81 (m, 12H).

Example 5

Example 5.1

1-bromo-4-(pentyloxy)benzene

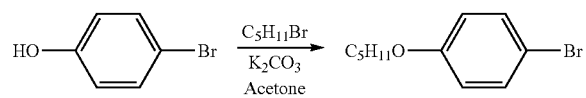

Example 5.1 is prepared similarly to example 3.1 to give 13.71 g (97.6% yield) as a clear oil. ¹H NMR (500 MHz, CDCl₃ (set to 7.26 ppm)) δ 7.357 (m, 2H), 6.771 (m, 2H), 3.913 (t, J=6.75 Hz, 2H), 1.773 (m, 2H), 1.475-1.325 (m, 4H), 0.931 (t, J=7.25, 3H).

Example 5.2

[4-(pentyloxy)phenyl]boronic acid

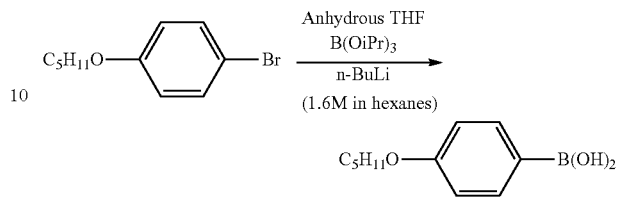

Example 5.2 is prepared similarly to example 3.2 to give 5.79 g (96.6% yield) as a white solid. For example 5.2, saturated ammonium chloride solution is added slowly to the completed and cooled, crude reaction mixture. A strong precipitation is observed. This is followed quickly by a phase separation of the water and THF and subsequent, significant resolution of the precipitate. Addition of a small, extra quantity of water resulted in complete solvation of all solids. The THF layer is removed and the water is washed twice with diethyl ether. The combined THF and diethyl ether phases are washed with brine, dried with magnesium sulfate, filtered, and the solvents are removed by rotary evaporation. Product is used in the next reaction without further purification.

Example 5.3

2,5-bis[4-(pentyloxy)phenyl]thiophene

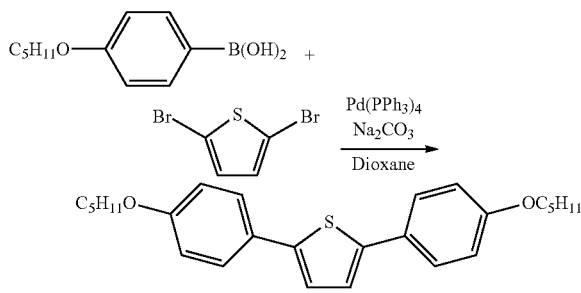

Example 5.3 is prepared similarly to example 3.3 to give 4.48 g (quantitative yield) as a pale yellow shiny solid. ¹H NMR (500 MHz, CDCl₃ (set to 7.26 ppm)) δ 7.525 (d (q), J=9.0 Hz, 4H), 7.135 (s, 2H), 6.906 (d (q), J=9.0 Hz, 4H), 3.983 (t, J=6.5 Hz, 4H), 1.804 (m, 4H), 1.50-1.35 (m, 8H), 0.942 (t, J=7.25, 6H).

Example 5.4

2,5-bis[4-(pentyloxy)phenyl]-1$\lambda^6$-thiophene-1,1-dione

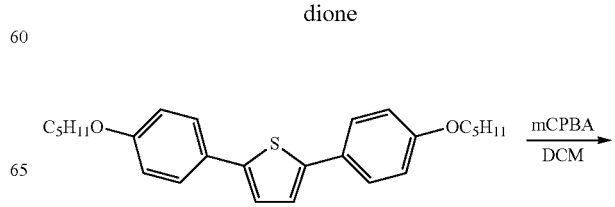

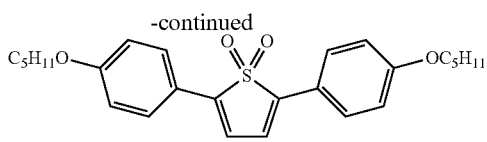

Example 5.4 is prepared similarly to example 3.4 to give 392 mg (9% yield) as a yellow solid. $^1$H NMR (500 MHz, CDCl$_3$ (set to 7.26 ppm)) δ 7.707 (d (q), J=9.0 Hz, 4H), 6.963 (d (q), J=9.0 Hz, 4H), 6.845 (s, 2H), 4.002 (t, J=6.5 Hz, 4H), 1.806 (m, 4H), 1.50-1.35 (m, 8H), 0.940 (t, J=7.0, 6H).

Example 5.5

Fullerene 5

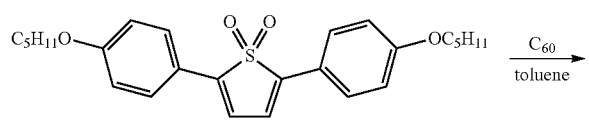

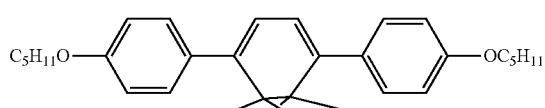

Example 5.5 is prepared similarly to example 3.5 to give 294 mg (30.1% yield) as a brown crystalline solid. Purity is confirmed by HPLC at 99.29%.

Example 6

Example 6.1

1-bromo-4-(heptyloxy)benzene

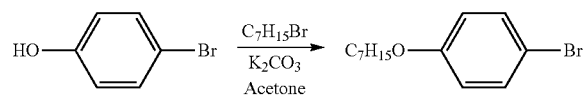

Example 6.1 is prepared similarly to example 3.1 to give 15.85 g (quantitative yield) as a clear oil. $^1$H NMR (500 MHz, CDCl$_3$ (set to 7.26 ppm)) δ 7.355 (m, 2H), 6.769 (m, 2H), 3.910 (t, J=6.5 Hz, 2H), 1.764 (m, 2H), 1.475-1.385 (m, 2H), 1.385-1.26 (m, 6H), 0.892 (t, J=6.75, 3H).

Example 6.2

[4-(heptyloxy)phenyl]boronic acid

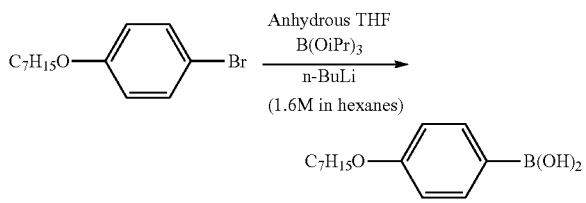

Example 6.2 is prepared similarly to example 3.2 to give ~7 g (quantitative yield) as a white solid. For example 6.2, saturated ammonium chloride solution is added slowly to the completed and cooled, crude reaction mixture. A strong precipitation is observed. This is followed quickly by a phase separation of the water and THF and subsequent, significant resolution of the precipitate. Addition of a small, extra quantity of water resulted in complete solvation of all solids. The THF layer is removed and the water is washed twice with diethyl ether. The combined THF and diethyl ether phases are washed with brine, dried with magnesium sulfate, filtered, and the solvents are removed by rotary evaporation. Product is used in the next reaction without further purification.

Example 6.3

2,5-bis[4-(heptyloxy)phenyl]thiophene

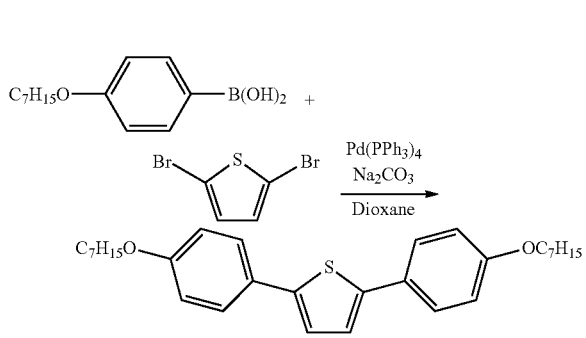

Example 6.3 is prepared similarly to example 3.3 to give 5.87 g (94.4% yield) as a pale grey shiny solid. $^1$H NMR (500 MHz, CDCl$_3$ (set to 7.26 ppm)) δ 7.524 (d (q), J=9.0 Hz, 4H), 7.135 (s, 2H), 6.906 (d (q), J=8.5 Hz, 4H), 3.982 (t, J=6.75 Hz, 4H), 1.796 (m, 4H), 1.51-1.42 (m, 4H), 1.41-1.26 (m, 12H), 0.899 (t, J=7.0, 6H).

Example 6.4

2,5-bis[4-(heptyloxy)phenyl]-1λ$^6$-thiophene-1,1-dione

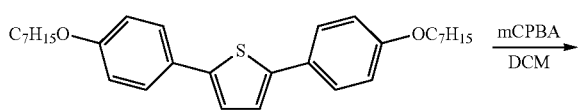

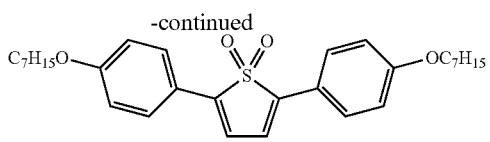

Example 6.4 is prepared similarly to example 3.4 to give 1.51 g (28% yield) as a yellow solid. $^1$H NMR (500 MHz, CDCl$_3$ (set to 7.26 ppm)) δ 7.707 (d (q), J=9.0 Hz, 4H), 6.962 (d (q), J=9.0 Hz, 4H), 6.844 (s, 2H), 4.000 (t, J=6.5 Hz, 4H), 1.798 (m, 4H), 1.50-1.41 (m, 4H), 1.40-1.25 (m, 12H), 0.899 (t, J=7.0, 6H).

Example 6.5

Fullerene 6

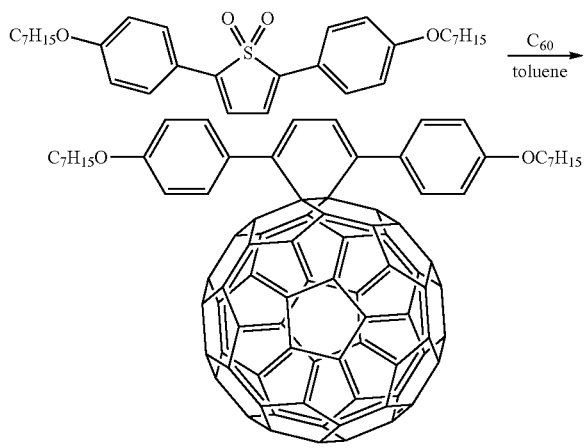

Example 6.5 is prepared similarly to example 3.5 to give 757 mg (65% yield) as a brown crystalline solid. Purity is confirmed by HPLC at 99.73%.

B) Use Examples

Example B1

Bulk Heterojunction Organic Photovoltaic Devices (OPVs) from Fullerenes C1, C2, 1-6

Organic photovoltaic (OPV) devices are fabricated on pre-patterned ITO-glass substrates (13 Ω/sq.) purchased from LUMTEC Corporation. Substrates are cleaned using common solvents (acetone, iso-propanol, deionized-water) in an ultrasonic bath. A conducting polymer poly(ethylene dioxythiophene) doped with poly(styrene sulfonic acid) [Clevios VPAI 4083 (H. C. Starck)] is mixed in a 1:1 ratio with deionized-water. This solution is filtered using a 0.45 μm filter before spin-coating to achieve a thickness of 20 nm. Substrates are exposed to ozone prior to the spin-coating process to ensure good wetting properties. Films are then annealed at 140° C. for 30 minutes in a nitrogen atmosphere where they are kept for the remainder of the process. Active material solutions (i.e. polymer+fullerene) are prepared to fully dissolve the solutes. Thin films are either spin-coated or blade-coated in a nitrogen atmosphere to achieve active layer thicknesses between 50 and 500 nm as measured using a profilometer. A short drying period follows to ensure removal of any residual solvent.

Typically, blade-coated films are dried at 70° C. for 2 minutes on a hotplate. For the last step of the device fabrication, Ca (30 nm)/Al (100 nm) cathodes are thermally evaporated through a shadow mask to define the cells. Current-voltage characteristics are measured using a Keithley 2400 SMU while the solar cells are illuminated by a Newport Solar Simulator at 100 mW·cm$^{-2}$ white light. The solar simulator is equipped with AM1.5G filters. The illumination intensity is calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV devices are prepared wherein the photoactive layer contains a blend of a polymer and a fullerene derivative of Examples 1 to 5, respectively, which is coated from a o-dichlorobenzene solution at a total solid concentration as shown in Table 1 below. The OPV device characteristics are shown in Table 1.

Polymer 1

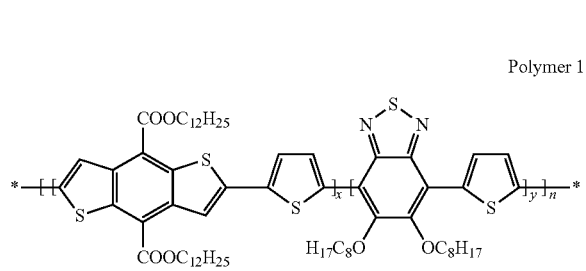

Polymer 1 and its preparation are disclosed in WO 2011/131280.

Polymer 2

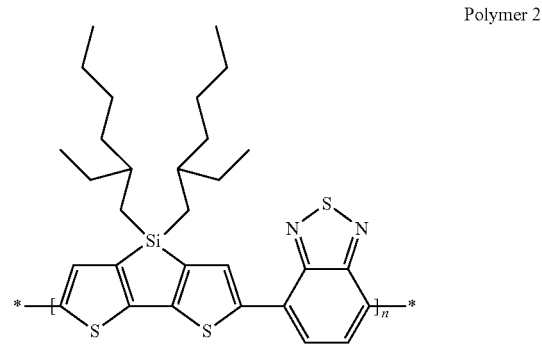 [SMILES: *c1cc2c(s1)-c1sc(-c3ccc(*)c4nsnc34)cc1[Si]2(CC(CC)CCCC)CC(CC)CCCC]

Polymer 2 and its preparation are disclosed in US 2008/006324.

TABLE 1

Photovoltaic cell characteristics.

| Fullerene | Polymer | ratio Polymer:Fullerene | conc$^n$ mg·ml$^{-1}$ | Voc mV | Jsc mA·cm$^{-2}$ | FF % | PCE % |
|---|---|---|---|---|---|---|---|
| C1 | 1 | 1.00:1.50 | 30 | 800 | −0.76 | 26.8 | 0.16 |
| C1 | 1 | 1.00:3.00 | 30 | — | — | — | —* |
| C2 | 1 | 1.00:1.50 | 30 | 807 | −1.00 | 27 | 0.22 |
| C2 | 1 | 1.00:3.00 | 30 | 720 | −1.86 | 21 | 0.36 |
| 1 | 1 | 1.00:1.50 | 30 | 900 | −8.33 | 39 | 3.0 |
| 1 | 1 | 1.00:3.00 | 30 | 920 | −6.26 | 62 | 3.6 |
| 1 | P3HT | 1.00:1.00 | 30 | 640 | −5.40 | 49 | 1.7 |
| 1 | 2 | 1.00:2.00 | 30 | 686 | −4.40 | 40 | 1.2 |
| 2 | 1 | 1.00:1.50 | 30 | 840 | −5.21 | 39 | 1.7 |
| 2 | 1 | 1.00:3.00 | 30 | 860 | −5.84 | 43 | 2.2 |
| 3 | 1 | 1.00:1.50 | 30 | 900 | −8.24 | 48 | 3.6 |
| 3 | 1 | 1.00:3.00 | 30 | 880 | −8.03 | 48 | 3.4 |
| 3 | P3HT | 1.00:1.00 | 30 | 680 | −5.98 | 53 | 2.2 |
| 3 | 2 | 1.00:2.00 | 30 | 690 | −5.38 | 34 | 1.3 |
| 4 | 1 | 1.00:1.50 | 30 | 860 | −8.72 | 45 | 3.4 |
| 4 | 1 | 1.00:3.00 | 30 | 860 | −6.87 | 56 | 3.1 |
| 5 | 1 | 1.00:1.50 | 30 | 900 | −7.15 | 45 | 2.9 |
| 5 | 1 | 1.00:3.00 | 30 | 899 | −8.92 | 48 | 3.8 |
| 6 | 1 | 1.00:1.50 | 30 | 868 | −4.25 | 42 | 1.5 |
| 6 | 1 | 1.00:3.00 | 30 | 898 | −9.47 | 43 | 3.7 |

*No working device

It can be seen that fullerene C1 and C2 of comparison example 1 and example 2, which has limited solubility in common organic solvent, prohibits the formation of the suitable morphology to achieve good performance in an OPV device, compared to fullerenes 1-6 according to the invention which show significantly better performance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

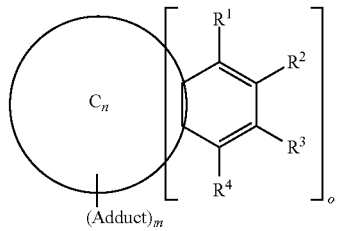

wherein $C_n$ is a fullerene composed of n carbon atoms, optionally with one or more atoms trapped inside, Adduct is a secondary adduct or a combination of secondary adducts appended to the fullerene $C_n$ with any connectivity, m is 0, an integer ≥1, or a non-integer >0, o is an integer ≥1, $R^1$, $R^2$, $R^3$, $R^4$ independently of each other denote H, halogen, CN, $R^5$ or $R^6$, $R^5$ denotes a saturated or unsaturated, non-aromatic carbo- or heterocyclic group, or an aryl, heteroaryl, aryloxy or heteroaryloxy group, wherein each of the aforementioned groups has 3 to 20 ring atoms, is mono- or polycyclic, does optionally contain fused rings, and is optionally substituted by one or more halogen atoms or CN groups, or by one or more identical or different groups $R^6$, $R^6$ denotes an alkyl group with 1 to 30 C atoms, which is straight-chain, branched or cyclic, and in which one or more $CH_2$ groups are each optionally replaced by —O—, —S—, —C(=O)—, —C(=S)—, —C(=O)—O—, —O—C(=O)—, —NR$^0$—, —C(=O)—NR$^0$—, —NR$^0$—C(=O)—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are each optionally replaced by F, Cl, Br, I or CN, $Y^1$ and $Y^2$ denote independently of each other H, F, Cl or CN, and $R^0$ and $R^{00}$ denote independently of each other H or an optionally substituted carbyl or hydrocarbyl group with 1 to 40 C atoms, wherein at least one of $R^1$, $R^2$, $R^3$ and $R^4$ denotes $R^5$ that is substituted by one or more groups $R^6$ as defined above, which have at least 3 C atoms wherein at least one $CH_2$ group is optionally replaced by —O—, —S—, —C(=O)—, —C(=S)—, —C(=O)—O—, —O—C(=O)—, —NR$^0$—, —SiR$^0$R$^{00}$—, —CF$_2$—, —CHR$^0$=CR$^{00}$—, —CY$^1$=CY$^2$— or —C≡C—.

2. The compound of claim 1, wherein n is 60, 70, 76, 78, 82, 84, 90, 94 or 96.

3. The compound of claim 2, wherein n is 60 or 70.

4. The compound of claim 1, wherein $C_n$ is a carbon based fullerene or an endohedral fullerene.

5. The compound of claim 4, wherein $C_n$ is selected from $(C_{60\text{-}Ih})$[5,6]fullerene, $(C_{70\text{-}D5h})$[5,6]fullerene, $(C_{76\text{-}D2*})$[5,6]fullerene, $(C_{84\text{-}D2*})$[5,6]fullerene, $(C_{84\text{-}D2d})$[5,6]fullerene, La@$C_{60}$, La@$C_{82}$, Y@$C_{82}$, Sc$_3$N@$C_{80}$, Y$_3$N@$C_{80}$, Sc$_3$C$_2$@$C_{80}$ or a mixture of two or more of the aforementioned fullerenes.

6. The compound according to claim 1, wherein $R^1$, $R^2$, $R^3$ and $R^4$ are independently of each other selected from H, halogen, CN, straight-chain, branched or cyclic alkyl with 1 to 30 C atoms, in which one or more CH$_2$ groups are each optionally replaced by —O—, —S—, —C(O)—, —C(S)—, —C(O)—O—, —O—C(O)—, —NR$^0$—, —SiR$^0$R$^{00}$—, or —CF$_2$—, or a carbocyclic or heterocyclic group selected from the following formulae
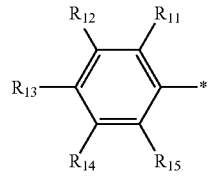
C-1
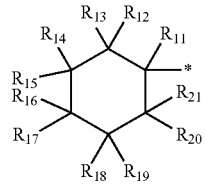
C-2
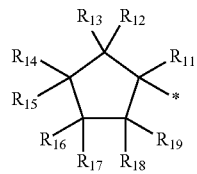
C-3
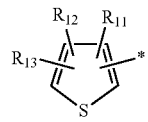
C-4
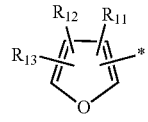
C-5
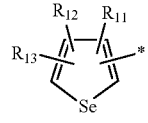
C-6
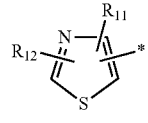
C-7
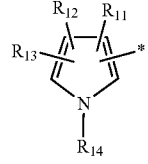
C-8
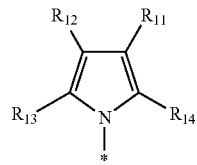
C-9
-continued
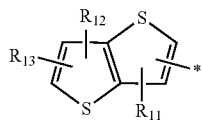
C-10
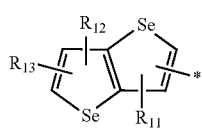
C-11
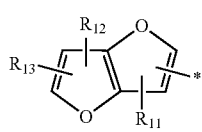
C-12
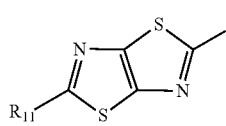
C-13
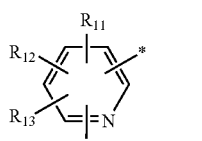
C-14
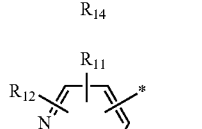
C-15
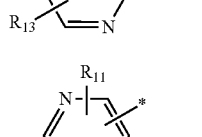
C-16
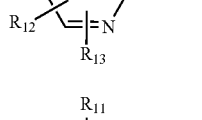
C-17
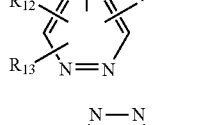
C-18
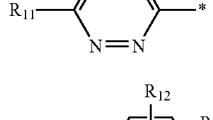
C-19
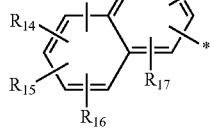
C-20
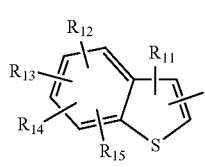

-continued

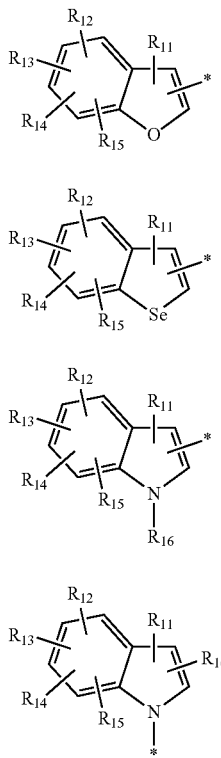

C-21

C-22

C-23

C-24 wherein

R⁰ and R⁰⁰ are as defined in claim 1,

R⁰⁰⁰ denotes an optionally substituted carbyl or hydrocarbyl group with 1 to 40 C atoms, $R^{11}, R^{12}, R^{13}, R^{14}, R^{15}, R^{16}, R^{17}$ and $R^{18}$ independently of each other denote H, halogen, CN, or an alkyl group with 1 to 30 C atoms, which is straight-chain, branched or cyclic, and in which one or more CH₂ groups are each optionally replaced by —O—, —S—, —C(=O)—, —C(=S)—, —C(=O)—O—, —O—C(=O)—, —NR⁰—, —C(=O)—NR⁰—, —NR⁰—C(=O)—, —SiR⁰R⁰⁰—, —CF₂—, —CHR⁰=CR⁰⁰—, —CY¹=CY²— or —C≡C— in such a manner that O and/or S atoms are not linked directly to one another, and in which one or more H atoms are each optionally replaced by F, Cl, Br, I or CN, and wherein in each of the aforementioned formulae at least one of $R^{11}, R^{12}, R^{13}, R^{14}, R^{15}, R^{16}, R^{17}$ and $R^{18}$ is different from H.

7. The compound according to claim 1, wherein R¹, R², R³ and R⁴ are independently of each other selected from H, straight-chain branched or cyclic alkyl with 1 to 30 C atoms, —O—, —COOR⁰⁰⁰, —COR⁰⁰⁰, CONR⁰R⁰⁰⁰, —F, —Cl, —NR⁰R⁰⁰⁰ or a carbocyclic or heterocyclic group selected from the following formulae

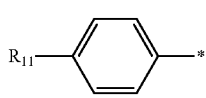

S-C-1

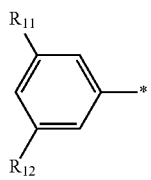

S-C-2

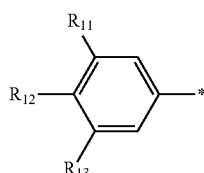

S-C-3

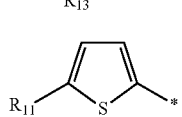

S-C-4

S-C-5

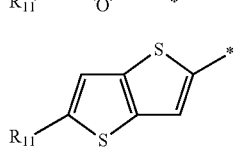

S-C-6

S-C-7

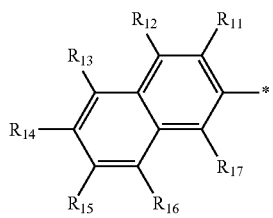

S-C-8

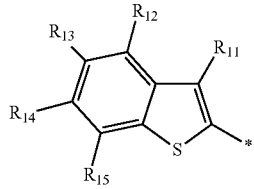

S-C-9

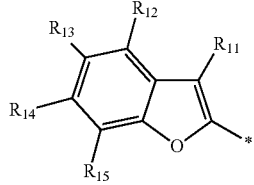

S-C-10 wherein

R⁰ and R⁰⁰ are as in claim 1,

R⁰⁰⁰ denoted an optionally substituted carbyl or hydrocarbyl group with 1 to 40 C atoms, $R^{11}, R^{12}, R^{13}, R^{14}, R^{15}, R^{16}, R^{17}$ and $R^{18}$ independently of each other denote H, halogen, CN, or an alkyl group with 1 to 30 C atoms, which is straight-chain, branched or cyclic, and in which one or more CH₂ groups are each optionally replaced by —O—, —S—, —C(=O)—, —C(=S)—, —C(=O)—O—, —O—C(=O)—, —NR⁰—, —C(=O)—NR⁰—, —NR⁰—C(=O)—, —SiR⁰R⁰⁰—, —CF₂—, —CHR⁰=CR⁰⁰—, —CY¹=CY²— or —C≡C— in such a manner that O and/or S atoms are not linked directly to one another, and in which one or more H atoms are each optionally replaced by F, Cl, Br, I or CN, and wherein in each of the aforementioned formulae at least one of $R^{11}$, $R^{12}$, $R^{13}$, $R^{14}$, $R^{15}$, $R^{16}$, $R^{17}$ and $R^{18}$ is different from H.

8. The compound according to claim 1, wherein $R^6$, on each occurrence identically or differently, is selected from straight-chain, branched or cyclic alkyl with 3 to 30 C atoms, in which one or more CH₂ groups are each optionally replaced by —O—, —S—, —C(O)—, —C(S)—, —C(O)—O—, —O—C(O)—, —NR⁰—, —SiR⁰R⁰⁰ or —CF₂—, and wherein one or more H atoms are each optionally replaced by fluorine atoms, wherein $R^0$ and $R^{00}$ are as defined in claim 1.

9. The compound of claim 1, wherein $R^0$ and $R^{00}$ denote H or an alkyl group with 1 to 12 C atoms.

10. The compound of claim 6, wherein $R^{000}$ denotes an alkyl group with 1 to 12 C atoms.

11. The compound of claim 1, wherein the fullerene $C_n$ is substituted at a [6,6] and/or [5,6] bond.

12. The compound of claim 1, wherein m is >0.

13. The compound of claim 12, wherein the secondary adduct is selected from the following formulae

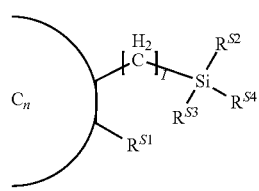

S-1

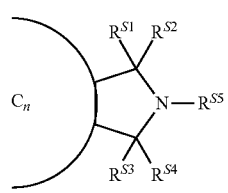

S-2

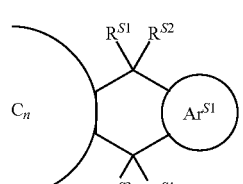

S-3

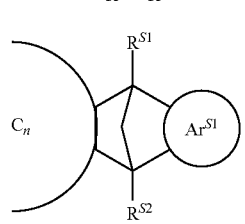

S-4

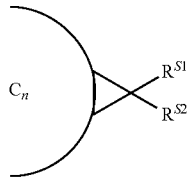

S-4

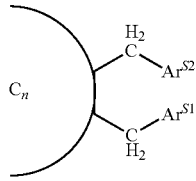

S-5

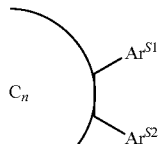

S-6

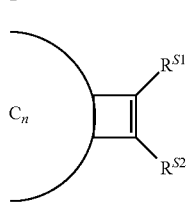

S-7

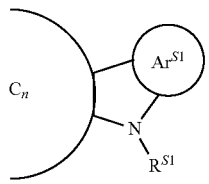

S-8

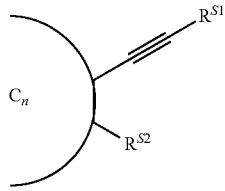

S-9

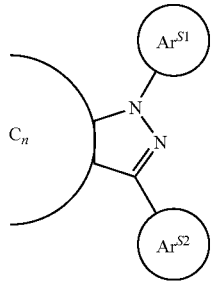

S-10 wherein
$R^{S1}$, $R^{S2}$, $R^{S3}$, $R^{S4}$ and $R^{S5}$ independently of each other denote H, halogen, CN, a saturated or unsaturated, non-aromatic carbo- or heterocyclic group, or an aryl, heteroaryl, aryloxy or heteroaryloxy group, wherein each of the aforementioned groups has 3 to 20 ring atoms, is mono- or polycyclic, does optionally contain fused rings, and is optionally substituted by one or more halogen atoms or CN groups, or by one or more identical or different groups $R^6$, or an alkyl group with 1 to 30 C atoms, which is straight-chain, branched or cyclic, and in which one or more $CH_2$ groups are each optionally replaced by —O—, —S—, —C(=O)—, —C(=S)—, —C(=O)—O—, —O—C(=O)—, —NR$^0$—, —C(=O)—NR$^0$—, —NR$^0$—C(=O)—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are each optionally replaced by F, Cl, Br, I or CN, Ar$^{S1}$ and Ar$^{S2}$ are independently of each other an aryl or heteroaryl group with 5 to 20 ring atoms, which is mono- or polycyclic, and which is substituted by one or more identical or different substituents R$^S$, R$^S$ denotes halogen or a straight-chain, branched or cyclic alkyl moiety with 1 to 30 C atoms, in which one or more $CH_2$ groups are optionally replaced by —O—, —S—, —C(O)—, —C(S)—, —C(O)—O—, —O—C(O)—, —S(O)$_2$—, —NR$^0$—, —SiR$^0$R$^{00}$—, —CF$_2$—, wherein R$^0$ and R$^{00}$ are as defined in claim 1.

14. A method which comprises operating an electronic device and utilizing a compound of claim 1 as electron acceptor or n-type semiconductor in a semiconducting material, organic electronic device or component of said organic electronic device.

15. A mixture comprising two or more fullerene compounds, one or more of which is a compound of claim 1.

16. A mixture comprising one or more compounds of claim 1 as electron acceptor or n-type semiconductor component, and further comprising one or more semiconducting compounds which have electron donor or p-type properties.

17. A mixture comprising one or more compounds of claim 1 and one or more p-type organic semiconductor compounds selected from conjugated organic polymers.

18. A mixture comprising one or more compounds of claim 1 and one or more compounds which are selected from compounds having one or more of a semiconducting, charge transport, hole transport, electron transport, hole blocking, electron blocking, electrically conducting, photoconducting and light emitting property.

19. A method which comprises operating an optical, electro-optical, electronic, electroluminescent, or photoluminescent device and utilizing a compound of claim 1 or a mixture thereof as a semiconducting, charge transport, electrically conducting, photoconducting, thermoelectric material or light emitting material in said optical, electro-optical, electronic, electroluminescent or photoluminescent device, or in a component of such a device or in an assembly comprising such a device or component.

20. A semiconducting, charge transport, electrically conducting, photoconducting, thermoelectric or light emitting material, which comprises a compound of claim 1 or a mixture thereof.

21. A formulation comprising one or more compounds of claim 1 or a mixture thereof, and further comprising one or more organic solvents.

22. An optical, electro-optical, electronic, electroluminescent, photoluminescent or thermoelectric device, or a component thereof, or an assembly comprising said device, prepared using a formulation of claim 21.

23. An optical, electro-optical, electronic, electroluminescent, photoluminescent or thermoelectric device, or a component thereof, or an assembly comprising said device, which comprises a compound of claim 1 or a mixture thereof.

24. An optical, electro-optical, electronic, electroluminescent, photoluminescent or thermoelectric device of claim 23 which is selected from organic field effect transistors (OFET), organic thin film transistors (OTFT), organic light emitting diodes (OLED), organic light emitting transistors (OLET), organic photovoltaic devices (OPV), organic photodetectors (OPD), organic solar cells, thermoelectric devices, laser diodes, Schottky diodes, photoconductors and photodetectors.

25. A component of an optical, electro-optical, electronic, electroluminescent, photoluinescent or thermoelectric device which comprises a compound of claim 1 or a mixture thereof, and which is selected from charge injection layers, charge transport layers, interlayers, planarising layers, antistatic films, polymer electrolyte membranes (PEM), conducting substrates and conducting patterns.

26. An assembly of claim 23, which is selected from the assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

27. A device according to claim 24, which is a bulk heterojunction (BHJ) OPV device or an inverted BHJ OPV device.

28. A bulk heterojunction which comprises, or is being formed from, a mixture of claim 17.

\* \* \* \* \*

UNITED STATES PATENT AND TRADEMARK OFFICE
CERTIFICATE OF CORRECTION

PATENT NO. : 9,543,523 B2
APPLICATION NO. : 14/483488
DATED : January 10, 2017
INVENTOR(S) : Nicolas Blouin et al.

It is certified that error appears in the above-identified patent and that said Letters Patent is hereby corrected as shown below:

In the Claims

Please correct Claim 25 to read as:
25. A component of an optical, electro-optical, electronic, electroluminescent, photoluminescent or thermoelectric device, which comprises a compound of claim 1 or a mixture thereof, and which is selected from charge injection layers, charge transport layers, interlayers, planarising layers, antistatic films, polymer electrolyte membranes (PEM), conducting substrates and conducting patterns.

Signed and Sealed this
Nineteenth Day of September, 2023

Katherine Kelly Vidal
*Director of the United States Patent and Trademark Office*